United States Patent
Urban et al.

(10) Patent No.: US 10,618,947 B2
(45) Date of Patent: Apr. 14, 2020

(54) DEVELOPMENT OF HBV-AND/OR HDV-SUSCEPTIBLE CELLS, CELL LINES AND NON-HUMAN ANIMALS

(71) Applicant: RUPRECHT-KARLS-UNIVERSITAET HEIDELBERG, Heidelberg (DE)

(72) Inventors: Stephan Urban, Neustadt/Weinstrasse (DE); Yi Ni, Heidelberg (DE)

(73) Assignee: RUPRECHT-KARLS-UNIVERSITÄT HEIDELBERG, Heidelberg (DE)

(*) Notice: Subject to any disclaimer, the term of this patent is extended or adjusted under 35 U.S.C. 154(b) by 0 days.

(21) Appl. No.: 14/442,279

(22) PCT Filed: Nov. 12, 2013

(86) PCT No.: PCT/EP2013/073602
§ 371 (c)(1),
(2) Date: May 12, 2015

(87) PCT Pub. No.: WO2014/072526
PCT Pub. Date: May 15, 2014

(65) Prior Publication Data
US 2015/0299289 A1  Oct. 22, 2015

Related U.S. Application Data

(60) Provisional application No. 61/725,144, filed on Nov. 12, 2012.

(51) Int. Cl.
| | | |
|---|---|---|
| C07K 14/705 | (2006.01) | |
| G01N 33/566 | (2006.01) | |
| C12N 15/12 | (2006.01) | |
| C12N 7/00 | (2006.01) | |
| A01K 67/027 | (2006.01) | |

(52) U.S. Cl.
CPC ............ *C07K 14/705* (2013.01); *C12N 7/00* (2013.01); *G01N 33/566* (2013.01); *A01K 67/0278* (2013.01); *A01K 2267/0337* (2013.01); *C12N 2730/10122* (2013.01); *C12N 2730/10152* (2013.01); *C12N 2760/10122* (2013.01); *C12N 2760/10152* (2013.01); *C12N 2999/005* (2013.01); *G01N 2333/02* (2013.01); *G01N 2333/08* (2013.01); *G01N 2333/188* (2013.01); *G01N 2500/02* (2013.01)

(58) Field of Classification Search
None
See application file for complete search history.

(56) References Cited

U.S. PATENT DOCUMENTS

| | | | | |
|---|---|---|---|---|
| 7,235,391 B2* | 6/2007 | Wu | ............ | A01N 1/02 |
| | | | | 435/235.1 |
| 2007/0105128 A1* | 5/2007 | Nakamura | ............ | C12Q 1/6876 |
| | | | | 435/6.11 |
| 2011/0059160 A1* | 3/2011 | Essner | ............ | C07K 14/00 |
| | | | | 424/450 |
| 2018/0044399 A1* | 2/2018 | Rajpal | ............ | C07K 14/70503 |

FOREIGN PATENT DOCUMENTS

| | | |
|---|---|---|
| CN | 102083967 A | 6/2011 |
| WO | WO 2013/159243 | 10/2013 |

OTHER PUBLICATIONS

Visser et al., Study of the transport of thyroid hormone by transporters of the SLC10 family. Molecular and Cellular Endocrinology 315 (2010) 138-145.*
Treichel et al., Receptor-mediated entry of hepatitis B virus particles into liver cells. Arch Virol (1997) 142: 493-498.*
Mortimer et al., Cationic lipid-mediated transfection of cells in culture requires mitotic activity. Gene Therapy (1999) 6, 403-411.*
Zou et al., Site-specific gene correction of a point mutation in human iPS cells derived from an adult patient with sickle cell disease. Blood. 2011;118(17):4599-4608.*
NCBI Reference Sequence NM_003049.3, Feb. 20, 2016, pp. 1-8.*
NCBI BLAST resutls Nov. 15, 2016, pp. 1-11.*
Golzio et al., Cell synchronization effect on mammalian cell permeabilization and gene delivery by electric field. Biochimica et Biophysica Acta 1563 (2002) 23-28.*
Rubinson et al., A lentivirus-based system to functionally silence genes in primary mammalian cells, stem cells and transgenic mice by RNA interference. Nature Genetics, 2003, 33:401-406 (Year: 2003).*
Hallen et al., Organization of the Membrane Domain of the Human Liver Sodium/Bile Acid Cotransporter. Biochemistry 2002, 41, 7253-7266 (Year: 2002).*

(Continued)

*Primary Examiner* — Christopher M Babic
*Assistant Examiner* — Arthur S Leonard
(74) *Attorney, Agent, or Firm* — Saliwanchik, Lloyd & Eisenschenk

(57) ABSTRACT

The present invention relates to a novel Hepatitis B virus (HBV) and/or Hepatitis D virus (HDV) receptor and its use for the development of cells, cell lines and non-human animals that are susceptible to HBV and/or HDV infection and can be used for immunological studies and/or for the screening of drugs, post-entry restriction factors and host dependency factors. It further relates to the use of the receptor for the identification of compounds useful in the treatment of HBV and/or HDV infection.

4 Claims, 9 Drawing Sheets

Figure 1:
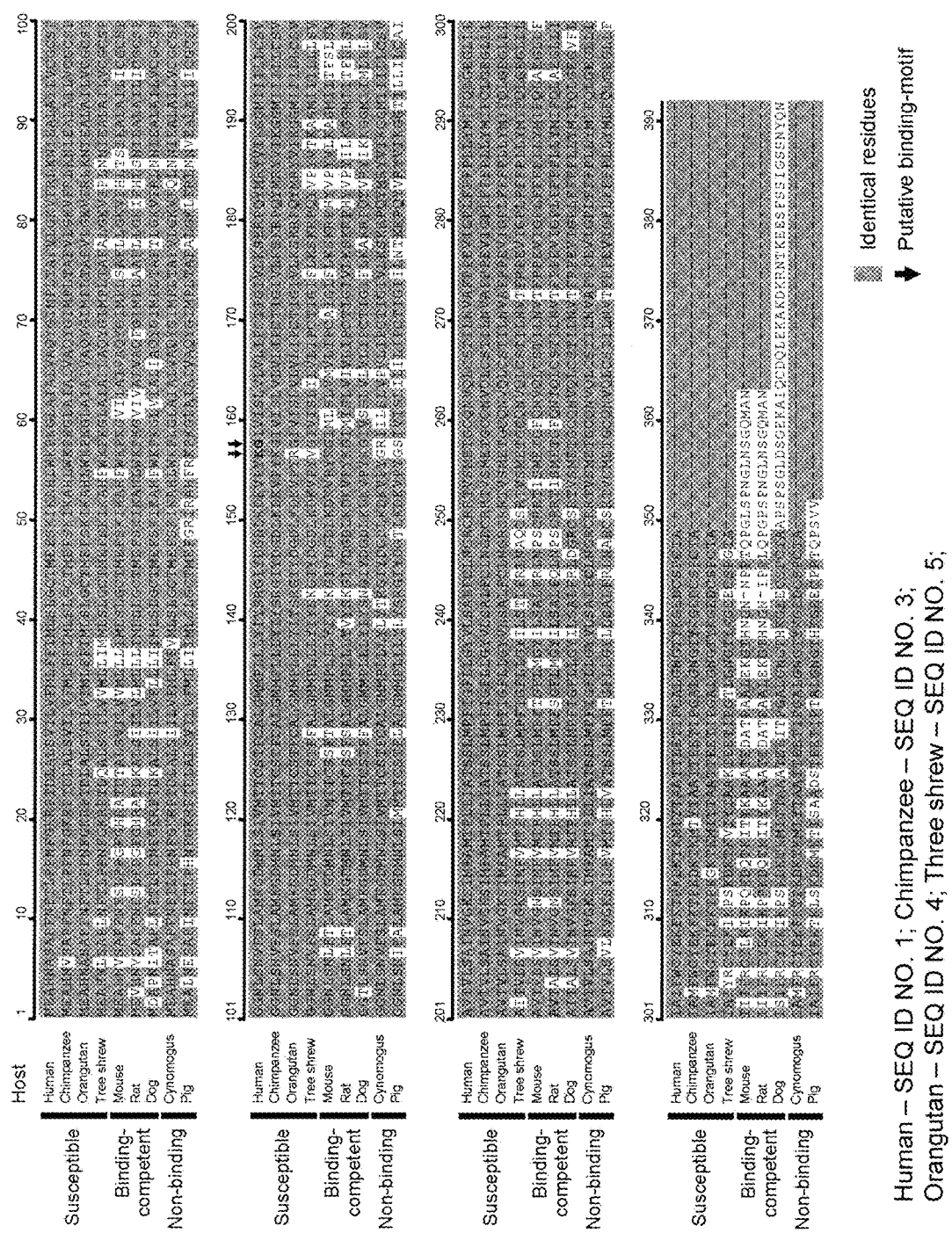

Specification includes a Sequence Listing.

(56) References Cited

OTHER PUBLICATIONS

Gripon et al., Infection of a human hepatoma cell line by hepatitis B virus. PNAS, 2002, 99: 15655-15660 (Year: 2002).*
Paran et al., HBV infection of cell culture: evidence for multivalent and cooperative attachment. EMBO J. 2001, 20:4443-4453. (Year: 2001).*
Khandelia et al., The impact of peptides on lipid membranes. Biochimica et Biophysica Acta 1778 (2008) 1528-1536 (Year: 2008).*
Sun et al., Sorting of rat liver and ileal sodium-dependent bile acid transporters in polarized epithelial cells. (1997) J. Cell Biol. 136, 1023-1035 (Year: 1997).*
Kim, Richard et al., "Modulation by Drugs of Human Hepatic Sodium-Dependent Bile Acid Transporter (Sodium Taurocholate Cotransporting Polypeptide) Activity," *The Journal Pharmacology and Experimental Therapeutics*, 1999, 291(3)1204-1209.
Yan, Huan et al., "Sodium taurocholate cotransporting polypeptide is a functional receptor for human hepatitis B and D virus," *eLIFE Sciences*, 2012, 1:1-28.
Anonymous, "Sodium ion-dosium taurocholate contransporter polypeptide is the functional receptor of human Hepatitis B. virus and Hepatitis D virus." China Basic Science, 2012, p. 8, No. 5.
Bijsmans, I. et al., "Sodium/bile acid contransporter [*Homo sapiens*], Genbank Accession." Jun. 27, 2012, No. NP_003040.
Cui, J. et al., "Sodium/bile acid contransporter [Mus musculus], Genbank Accession." Sep. 1, 2012, No. NP_001171032.
Hagenbuch, B. et al., "Molecular Cloning, Chromosomal Localization, and Functional Characterization of a Human Liver Na =/Bile Acid Contransporter." J. Clin. Ivnest., Mar. 1994, pp. 1326-1331, vol. 93.
Wen-Hui, L. et al., "Chinese scientists have found the functional receptor of Hepatitis B virus and Hepatitis D virus." Chinese Basic Science, pp. 8, 11-17, 19-24, No. 5.
Miura, T. et al., "sodium/bile acid contransporter [Rattus norvegicus], Genbank Accccession." Sep. 8, 2012, No. NP_058743.
NCBI predicted, "sodium/bile acid contransporter [Pan troglodytes], Genbank Accession." Oct. 25, 2012, No. XP_510035.
NCBI predicted, "sodium/bile acid contransporter [Pongo abelii], Genbank Accession." Aug. 17, 2012, No. XP_002824936.
NCBI predicted, sodium/bile acid contransporter isoform 1 [Canis lupus familiaris], Dec. 2, 2011, No. XP_537494.
Li, W., et al., "Sodium ion-sodium taurocholate cotransporter polypeptide is the functional receptor of human Hepatitis B virus and Hepatitis D virus." China Basic Science, Oct. 15, 2012, No. 5, p. 8.
Decision of Rejection issued by the Chinese Patent Office dated Jan. 29, 2019, for Chinese Patent Application No. 201380059075.0, 19 pages.
Li, W., et al., "Sodium ion-sodium taurocholate cotransporter polypeptide is the functional receptor of human Hepatitis B virus and Hepatitis D virus." China Basic Science, Oct. 15, 2012, 5: 8.
Din, C. et al. "Animal Models of Common and Emerging Infectious Diseases," China Union Medical University Press, Jan. 31, 2012, p. 128.

* cited by examiner

DEVELOPMENT OF HBV-AND/OR HDV-SUSCEPTIBLE CELLS, CELL LINES AND NON-HUMAN ANIMALS

CROSS REFERENCE TO A RELATED APPLICATION

This application is a National Stage Application of International Application Number PCT/EP2013/073602, filed Nov. 12, 2013; which claims the benefit of U.S Provisional Patent Application Ser. No. 61/725,144, filed Nov. 12, 2012; both of which are incorporated herein by reference in their entirety.

The Sequence Listing for this application is labeled "SEQ-LIST-4-24-15.TXT," which was created on Apr. 27, 2015, and is 30 KB. The entire content is incorporated herein by reference in its entirety.

The present invention relates to a novel Hepatitis B virus (HBV) and/or Hepatitis D virus (HDV) receptor and its use for the development of cells, cell lines and non-human animals that are susceptible to HBV and/or HDV infection and can be used for immunological studies and/or for the screening of drugs, post-entry restriction factors and host dependency factors. It further relates to the use of the receptor for the identification of compounds useful in the treatment of HBV and/or HDV infection.

The human hepatitis B virus (HBV) causes acute and chronic liver infections. 350 million people are persistently infected (Cornberg et al., *Minerva Gastroenterol Dietol* 2010, 56(4), 451-465). Chronic hepatitis B will remain a major global health problem, despite the availability of vaccines. Therapies (IFNα and five nucleoside analogues) are limited and mostly non-curative.

HBV is a member of the hepadnaviridae. Hepadnaviruses are the smallest enveloped DNA viruses which replicate via reverse transcription of a pgRNA intermediate. During assembly the nucleocapsid acquires three viral envelope proteins termed large (L), middle (M) and small (S). They are encoded in one open reading frame and share the S-domain which is required for membrane anchoring. In addition to the S-domain, M contains an N-terminal hydrophilic extension of 55 amino acids (preS2), while L is further extended by 107, 117 or 118 amino acids (genotype-dependent) termed preS1 (Urban, *Future Virol.* 2008, 3(3), 253-264). The hepatitis D virus (HDV) is a satellite virusoid utilizing the HBV envelope proteins for entry into hepatocytes. The myristoylated preS1-domain of L is known to play the key role in HBV and HDV infectivity.

Hepadnaviruses show pronounced species specificities. The fact that mice and rats are refractory to HBV has been attributed to the lack of either (an) entry factor(s) or the presence of post entry restriction factors. Since delivery of plasmid-encoded HBV-genomes into hepatic cells of non-susceptible species promote virion secretion, it is assumed that host constraints are related to early infection events. Another peculiarity of HBV is the efficacy to selectively infect hepatocytes in vivo. The hypothesis that the species specificity and the extraordinary liver tropism are associated with an early step of HBV infection, e.g. specific receptor recognition, is attractive.

Currently only primary human (PHH), primary tupeia belangeri (PTH) hepatocytes and differentiated HepaRG cells support the complete HBV replication cycle. The latter is a hepatic progenitor cell line capable of differentiation into PHH-like cells following DMSO treatment. Primary mouse (PMH) and primary rat hepatocytes (PRH) are refractory to HBV. Accordingly, mice and rats do neither support de novo HBV infection nor virus spread. The lack of a (immune competent) small animal model is a major obstacle in HBV research demanding for the elucidation of the underlying molecular restriction factors. It lead to the development of surrogate systems like HBV-transgenic mice, bearing an integrate of an over-length HBV genome, or immune-deficient PHH-transplanted uPA/Scid mice.

The inventors have previously identified HBV L-protein derived lipopeptides that block HBV and HDV infection of PHH and HepaRG cells (Gripon et al., *J Virol* 2005, 79(3), 1613-1622; Schulze et al., *J Virol* 2010, 84(4), 1989-2000; WO 2009/092611 A1). They represent the N-terminal 47 amino acids of the preS1-domain of HBV (HBVpreS/2-48$_{myr}$) and include the naturally occurring modification with myristic acid. Since preincubation of cells with HBVpreS/2-48$_{myr}$ blocks infection they presumably address a receptor, which, however, is so far unknown.

Accordingly, it was an object of the present invention to identify the receptor responsible for the binding of these HBV L-protein derived lipopeptides.

It was a further object of the present invention to develop cells and cell lines that are susceptible to HBV and/or HDV infection through expression of said receptor.

It was yet a further object of the present invention to provide a non-human transgenic animal that is susceptible to HBV and/or HDV infection.

Such transgenic cells, cell lines and animals could then be used for immunological studies and/or for the screening of drugs, post-entry restriction factors and host dependency factors.

Furthermore, the newly identified receptor could be used to identify further compounds useful in the treatment of HBV and/or HDV infection.

The objects of the present invention are solved by a Hepatitis B virus (HBV) or Hepatitis D virus (HDV) receptor having
(a) an amino acid sequence represented by SEQ ID NO: 1, or
(b) an amino acid sequence comprising
SEQ ID NO:2 or an amino acid sequence which is at least 90%, preferably at least 91%, more preferably at least 92%, identical to SEQ ID NO:2, and
an amino acid sequence having the general formula Pro-Tyr-X-Gly-Ile [SEQ ID NO: 11], wherein X is selected from Lys, Arg and Val.

The objects of the present invention are also solved by a Hepatitis B virus (HBV) or Hepatitis D virus (HDV) receptor having
(a) an amino acid sequence represented by SEQ ID NO: 1, or
(b) an amino acid sequence comprising
SEQ ID NO:2 or an amino acid sequence which is at least 90%, preferably at least 91%, more preferably at least 92%, identical to SEQ ID NO: 2, and
having Gly in the position corresponding to amino acid 158 of SEQ ID NO: 1 or
having the sequence Gly-Ile in the position corresponding to amino acids 158 and 159 of SEQ ID NO:1.

SEQ ID NO: 1 is the human sodium taurocholate cotransporter polypeptide NTCP/SLC10A1.

In preferred embodiments of the present invention, "an amino acid sequence represented by SEQ ID NO: 1" refers to an amino acid sequence which is at least 90%, preferably at least 91%, more preferably at least 92%, more preferably at least 95% or 99% identical to SEQ ID NO: 1 or is identical to SEQ ID NO: 1.

Said amino acid sequence (b) preferably comprises two regions or domains:
(1) a region or domain comprising the amino acids 265 to 291 of human NTCP (or sequences with at least 90, 91 or 92% identity)

QLCSTILNVAFPPEVIGPLFFFPLLYM; [SEQ ID NO: 2]

(2) a region or domain comprising an amino acid sequence having the general formula

PYXGI, [SEQ ID NO: 11]

wherein X is selected from K, R and V.

In one embodiment, the region or domain (2) of said amino acid sequence (b) comprises (at least)
- a Gly, which is in a/the position corresponding to amino acid 158 of SEQ ID NO:1, such as in the amino acid sequence with the general formula PYXGI [SEQ ID NO.: 11];
or
- comprises or has the sequence Gly-Ile in a/the position corresponding to amino acids 158 and 159 of SEQ ID NO: 1,
    such as in the amino acid sequence with the general formula PYXGI [SEQ ID NO.: 11].

In one embodiment, said amino acid sequence (b) does not comprise more than 450 amino acids, preferably not more than 400 amino acids.

In one embodiment, said amino acid sequence (b) further comprises the amino acid sequence Gly-Met-Ile-Ile-Ile-Leu-Leu [SEQ ID NO: 12].

In this embodiment, said amino acid sequence (b) comprises three regions or domains:
(1) a region or domain comprising the amino acids 265 to 291 of human NTCP (or sequences with at least 90, 91 or 92% identity)

QLCSTILNVAFPPEVIGPLFFFPLLYM; [SEQ ID NO: 2]

(2) a region or domain comprising an amino acid sequence having the general formula

PYXGI, [SEQ ID NO: 11]

wherein X is selected from K, R and V.
(3) a region or domain comprising an amino acid sequence

GMIIILL. [SEQ ID NO: 12]

The objects of the present invention are also solved by a HBV or HDV receptor as defined above having an amino acid sequence selected from the group consisting of SEQ ID NO:1 and SEQ ID NOs:3 to 8.

The objects of the present invention are also solved by an isolated nucleic acid sequence, preferably DNA sequence, encoding a HBV or HDV receptor as defined above.

The objects of the present invention are also solved by a vector comprising the nucleic acid sequence as defined above.

In one embodiment, said vector is a viral transfer vector, preferably selected from the group consisting of lentivirus vectors, retrovirus vectors, herpesvirus vectors, adenovirus vectors, baculovirus vectors and adeno-associated virus (AAV) vectors. Lentivirus vectors allow to produce stable cell lines, adenovirus vectors and AAVs are useful in transducing primary hepatocytes in vitro or mice in vivo and render them transiently susceptible to HBV and/or HDV infection.

The objects of the present invention are also solved by a host cell comprising the vector as defined above or comprising the nucleic acid sequence as defined above, which has been artificially introduced into said host cell.

In one embodiment, the term "artificially introduced" refers to the fact that the nucleic acid sequence is expressed under the control of a non-endogenous promoter, e.g. a promoter that is naturally not affiliated with said nucleic acid sequence in said host cell.

Particular preferred cells according to the present invention are cancer cell lines, stem cell lines and primary hepatocytes, wherein, preferably, said cancer cell lines are selected from hepatoma cell lines, e.g. human, mouse or rat hepatoma cell lines. Preferred human hepatoma cell lines include HuH7, HepG2 and HepaRG. Preferred mouse hepatoma cell lines include Hep56.1D and Hepa1-6. In one embodiment, said primary hepatocytes are immortalized.

The objects of the present invention are also solved by a transgenic cell or cell line comprising one or more transgenes, wherein one of said one or more transgenes is the nucleic acid sequence as defined above, thereby making said transgenic cell or cell line susceptible to HBV and/or HDV infection or increasing the susceptibility of said transgenic cell or cell line to HBV and/or HDV infection or allowing said transgenic cell or cell line to bind HBV and/or HDV.

The objects of the present invention are also solved by a non-human transgenic animal comprising one or more transgenic cells or cell lines as defined above or comprising one or more transgenes, wherein one of said one or more transgenes is the nucleic acid sequence as defined above, thereby
making said transgenic animal susceptible to HBV and/or HDV infection or increasing the susceptibility of said transgenic animal to HBV and/or HDV infection.

Preferred non-human transgenic animals in accordance with the present invention are selected from the group consisting of mouse, rat, rabbit, guinea pig and non-human primates, such as cynomolgus monkey and rhesus monkey. A particular preferred transgenic animal is a mouse.

In one embodiment, said non-human transgenic animal is immune-competent.

The objects of the present invention are also solved by a hepatocyte isolated from the non-human transgenic animal as defined above.

The objects of the present invention are also solved by a method for producing a cell that is susceptible to HBV and/or HDV infection, or has an increased susceptibility to HBV and/or HDV infection, or is able to bind HBV and/or HDV, said method comprising the steps of
- providing a cell that is non-susceptible to HBV and/or HDV infection or has a low susceptibility to HBV and/or HDV infection or is unable to bind HBV and/or HDV; and
- transfecting or transducing said cell with the nucleic acid sequence as defined above or with the vector as defined above.

In one embodiment, said cell is non-susceptible to HBV and/or HDV infection or is unable to bind HBV and/or HDV.

In one embodiment, the method further comprises the step of adding a cell-cycle arresting or differentiation inducing agent to said cell, prior to said step of transfecting or transducing said cell.

In one embodiment, said cell-cycle arresting or differentiation inducing agent is DMSO, wherein, preferably, DMSO is added to a final concentration in the range of from 0.1 to 5% (v/v), more preferably 0.5 to 2.5% (v/v).

In one embodiment, the method further comprises the step of knocking-out or knocking-down one or more endogenous genes of said cell.

In one embodiment, said endogenous gene of said cell is the gene encoding the natural NTCP/SCL10A1 polypeptide of said cell (i.e. a homolog of human NTCP/SCL10A1, which does not make said cell susceptible to HBV and/or HDV infection and/or does not allow said cell to bind HBV and/or HDV). Such knock-out or knock-down helps to prevent a dominant negative effect of the endogenous (non-human) gene.

In one embodiment, said knocking-out or knocking-down of one or more endogenous genes of said cell is achieved by means of an shRNA-vector. In one embodiment both the nucleic acid sequence as defined above and the shRNA are contained in a single vector.

In one embodiment, said method further comprises the step of immortalizing said cell to obtain a stable cell line of said cell.

In one embodiment, said cell is selected from a hepatoma cell line, e.g. human hepatoma cell lines, such as HuH7, HepG2 and, in particular, HepaRG. In another embodiment, said cell is a primary hepatocyte.

The objects of the present invention are also solved by a method of producing a cell that is susceptible to HBV and/or HDV infection, said method comprising the steps of providing a cell that is non-susceptible to HBV and/or HDV infection; and modifying the endogenous gene of said cell corresponding to the human gene encoding SEQ ID NO: 1 by homologous recombination, so as to replace the amino acids corresponding to amino acids 192 to 200, preferably amino acids 194 to 197, of SEQ ID NO: 1 with amino acids 192 to 200, preferably amino acids 194 to 197, of SEQ ID NO: 1 or SEQ ID NO:5 and/or the amino acids corresponding to amino acids 155 to 165, preferably amino acids 156 to 162, of SEQ ID NO: 1 with amino acids 155 to 165, preferably amino acids 156 to 162, of SEQ ID NO: 1, SEQ ID NO:4 or SEQ ID NO: 5.

Without wishing to be bound by a certain theory, the present inventors believe that the region corresponding to amino acids 155 to 165, and in particular amino acids 157 and 158 (Gly), are involved in the binding of HBV and/or HDV, whereas the region corresponding to amino acids 192 to 200, and in particular amino acids 195 to 197 (Ile-Leu-Leu), are involved in HBV and/or HDV infection (e.g. by mediating a cell entry step, such as membrane fusion).

The objects of the present invention are also solved by a cell obtained by the above methods and by a non-human transgenic animal, e.g. a mouse (such as a uPA/Scid mouse), comprising at least one such cell.

The objects of the present invention are also solved by the use of (a) an amino acid sequence represented by SEQ ID NO: 1, or (b) an amino acid sequence comprising SEQ ID NO: 2 or a an amino acid sequence which is at least 90%, preferably at least 91%, more preferably at least 92%, identical to SEQ ID NO: 2, and an amino acid sequence having the general formula Pro-Tyr-X-Gly-Ile [SEQ ID NO: 11], wherein X is selected from Lys, Arg and Val as a receptor for HBV or HDV.

In preferred embodiments of the present invention, "an amino acid sequence represented by SEQ ID NO: 1" refers to an amino acid sequence which is at least 90%, preferably at least 91%, more preferably at least 92%, more preferably at least 95% or 99% or is identical to SEQ ID NO: 1.

Other embodiments of amino acid sequence (b) as defined above may also be used.

In one embodiment, said use comprises the steps of exposing a first cell, which expresses said amino acid sequence, to a compound known to bind to said receptor for HBV or HDV and measuring a response of said cell;

exposing a second cell of the same type of said first cell, which expresses said amino acid sequence, to a candidate compound suspected of binding to said receptor for HBV or HDV and measuring a response of said second cell; and comparing the response of said cell and the response of said second cell and determining whether or not said candidate compound binds to said receptor for HBV or HDV based on such comparison.

Compounds known to bind to said receptor for HBV or HDV include certain HBV preS-derived lipopeptides, as, for example, defined in WO 2009/092611 A1.

The objects of the present invention are also solved by a method for identifying a compound useful in the treatment of HBV and/or HDV infection, said method comprising the step of identifying a compound that binds to the HBV and/or HDV receptor as defined above and/or inhibits binding of HBV and/or HDV to the HBV and/or HDV receptor as defined above.

The objects of the present invention are also solved by a compound that binds to the HBV and/or HDV receptor as defined above and/or inhibits binding of HBV and/or HDV to the HBV and/or HDV receptor as defined above for use in the treatment of HBV and/or HDV infection, wherein said compound is not a HBV L-protein derived lipopeptide or a natural substrate or binding partner of said HBV and/or HDV receptor (e.g. naturally occurring bile salts, such as sodium taurocholate).

The objects of the present invention are also solved by the use of a compound as defined above in the manufacture of a medicament for the treatment of HBV and/or HDV infection.

The objects of the present invention are also solved by a method of treatment of HBV and/or HDV infection comprising the administration of a compound as defined above to a subject in need thereof.

In one embodiment, said compound is selected from the group consisting of (poly-)peptides, antibodies, aptamers and organic compounds, such as small molecules and peptidomimetic compounds. Useful organic compounds may also include derivatives of bile salts.

The term "small molecules", as used herein, is meant to refer to non-polymeric low molecular weight organic compounds.

In one embodiment, said compound binds to the HBV and/or HDV receptor as defined above at a site corresponding approximately to amino acids 155 to 165, preferably amino acids 156 to 162, of SEQ ID NO:1.

The objects of the present invention are also solved by the use of
a host cell as defined above, or
a transgenic cell or cell line as defined above, or
a hepatocyte as defined above, or
a cell according as defined above, or
a non-human transgenic animal as defined above
for immunological studies and/or for the screening of drugs, post-entry restriction factors or host dependency factors.

SEQ ID NOs:1 to 10 refer to the following sequences:

(Human NTCP)
SEQ ID NO: 1
MEAHNASAPFNFTLPPNFGKRPTDLALSVILVFMLFFIMLSLGCTMEFSK

IKAHLWKPKGLAIALVAQYGIMPLTAFVLGKVFRLKNIEALAILVCGCSP

GGNLSNVFSLAMKGDMNLSIVMTTCSTFCALGMMPLLLYIYSRGIYDGDL

KDKVPYKGIVISLVLVLIPCTIGIVLKSKRPQYMRYVIKGGMIIILLCSV

AVTVLSAINVGKSIMFAMTPLLIATSSLMPFIGFLLGYVLSALFCLNGRC

RRTVSMETGCQNVQLCSTILNVAFPPEVIGPLFFFPLLYMIFQLGEGLLL

IAIFWCYEKFKTPKDKTKMIYTAATTEETIPGALGNGTYKGEDCSPCTA

SEQ ID NO: 2
(amino acids 265 to 291 of Human NTCP)
QLCSTILNVAFPPEVIGPLFFFPLLYM

SEQ ID NO: 3
(Chimpanzee NTCP)
MEAHNVSAPFNFTLPPNFGKRPTDLALSVILVFMLFFIMLSLGCTMEFSK

IKAHLWKPKGLAIALVAQYGIMPLTAFVLGKVFRLKNIEALAILVCGCSP

GGNLSNVFSLAMKGDMNLSIVMTTCSTFCALGMMPLLLYIYSRGIYDGDL

KDKVPYKGIVISLVLVLIPCTIGIVLKSKRPQYMRYVIKGGMIIILLCSV

AVTVLSAINVGKSIMFAMTPLLIATSSLMPFIGFLLGYVLSALFCLNGRC

RRTVSMETGCQNVQLCSTILNVAFPPEVIGPLFFFPLLYMIFQLGEGLLL

IAMFWCYEKFKTPKDKTKMTYTAATTEETIPGALGNGTYKGEDCSPCTA

SEQ ID NO: 4
(Orang-utan NTCP)
MEAHNASAPFNFTLPPNFGKRPTDLALSVILVFMLFFIMLSLGCTMEFSK

IKAHLWKPKGLAIALVAQYGIMPLTAFVLGKVFRLKNIEALAILVCGCSP

GGNLSNVFSLAMKGDMNLSIVMTTCSTFCALGMMPLLLYIYSRGIYDGDL

KDKVPYRGIVISLVLVLIPCTIGIVLKSKRPQYVPYVIKGGMIIILLCSV

AVTVLSAINVGKSIMFAMTPLLIATSSLMPFIGFLLGYVLSALFCLNGRC

RRTVSMETGCQNVQLCSTILNVAFPPEVIGPLFFFPLLYMIFQLGEGLLL

IAMFWCYEKFKTPKGKTKMIYTAATTEETIPGALGNGTYKGEDCSPCTA

SEQ ID NO: 5
(*Tupaia belangeri*/Tree shrew NTCP)
MEAHNLSAPLNFTLPPNFGKRPTDQALSVILVVMLLIMMLSLGCTMEFSK

IKAHFWKPKGLAIALLAQYGIMPLTAFALGKVFPLNNIEALAILVCGCSP

GGNLSNVFSLAMKGDMNLSIVMTTCSTFFALGMMPLLLYIYSKGIYDGDL

KDKVPYVGIVISLILVLIPCTIGIFLKSKRPQYVPYVTKAGMIIILLLSV

AITVLSVINVGKSIMFVMTPHLLATSSLMPFIGFLLGYILSTLFRLNAQC

SRTVSMETGCQNVQLCSTILNVTFRPEVIGPLFFFPLLYMIFQLGEGLLL

IAIYRCYEKIKPSKDKTKVIYTAAKTEETIPGTLGNGTYKGEECSPGTA

SEQ ID NO: 6
(Mouse NTCP)
MEAHNVSAPFNFSLPPGFGHRATDTALSVILVVMLLLIMLSLGCTMEFSK

IKAHFWKPKGVIIAIVAQYGIMPLSAFLLGKVFHLTSIEALAILICGCSP

GGNLSNLFTLAMKGDMNLSIVMTTCSSFTALGMMPLLLYIYSKGIYDGDL

KDKVPYKGIMLSLVMVLIPCAIGIFLKSKRPHYVPYVLKAGMIITFSLSV

AVTVLSVINVGNSIMFVMTPHLLATSSLMPFTGFLMGYILSALFRLNPSC

RRTISMETGFQNVQLCSTILNVTFPPEVIGPLFFFPLLYMIFQLAEGLLF

IIIFRCYLKIKPQKDQTKITYKAAATEDATPAALEKGTHNGNNPPTQPGL

SPNGLNSGQMAN

SEQ ID NO: 7
(Rat NTCP)
MEVHNVSAPFNFSLPPGFGHRATDKALSIILVLMLLLIMLSLGCTMEFSK

IKAHLWKPKGVIVALVAQFGIMPLAAFLLGKIFHLSNIEALAILICGCSP

GGNLSNLFTLAMKGDMNLSIVMTTCSSFSALGMMPLLLYVYSKGIYDGDL

KDKVPYKGIMISLVIVLIPCTIGIVLKSKRPHYVPYILKGGMIITFLLSV

AVTALSVINVGNSIMFVMTPHLLATSSLMPFSGFLMGYILSALFQLNPSC

RRTISMETGFQNIQLCSTILNVTFPPEVIGPLFFFPLLYMIFQLAEGLLI

IIIFRCYEKIKPPKDQTKITYKAAATEDATPAALEKGTHNGNIPPLQPGP

SPNGLNSGQMAN

SEQ ID NO: 8
(Dog NTCP)
MDAPNITAPLNFTLPPNFGKRPTDKALSIILVFLLLIIMLSLGCTMEFSK

IKAHFWKPKGLVIALIAQYGIMPLTAFTLGKVFRLNNIEALAILVCGCSP

GGTLSNVFSLAMKGDMNLSIVMTTCSTFFALGMMPLLLYIYSNGIYDGDL

KDKVPYKGIVSSLVLVLIPCTIGIFLKAKRPQYVRYIKKGGMIIMLLLSV

AITALSVINVGKSIRFVMTPHLLATSSLMPFIGFLLGYILSALFRLDGRC

SRTVSMETGCQNVQLCSTILNVTFPPEVIGPLFFFPLLYMIFQLGEGVFL

ISIFRCYEKIKPSKDKTKMIYTAAATEEITPGALGNTHKGEECSPCTAA

PSPSGLDSGEKAIQCDQLEKAKDKRNTKEESFSSIGSSNYQN

SEQ ID NO: 9
(Cynomolgus NTCP)
MEAHNASAPFNFTLPPNFGKRPTDLALSIILVFMLFFVMLSLGCTMEFSK

IKAHLWKPKGLAIALVAQYGIMPLTAFVLGKVFQLNNIEALAILVCGCSP

GGNLSNVFSLAMKGDMNLSIVMTTCSTFCALGMMPLLLYLYTRGIYDGDL

KDKVPYGRIILSLVPVLIPCTIGIVLKSKRPQYMRYVIKGGMIIILLCSV

AVTVLSAINVGKSIMFAMTPLLIATSSLMPFIGFLLGYVLSALFCLNGRC

RRTVSMETGCQNVQLCSTILNVAFPPEVIGPLFFFPLLYMIFQLGEGLLL

IAMFRCYEKFKTPKDKTKMIYTAATTEETIPGALGNGTYKGEDCSPCTA

SEQ ID NO: 10
(Pig NTCP)
MEALNESAPINFTLPHNFGKRPTDLALSVILVFMLLIIMLSLGCTMEFGR

IRAHFRKPKGLAIALVAQYGIMPLTAFALGKLFRLNNVEALAILICGCSP

-continued

```
GGNLSNIFALAMKGDMNLSIMMTTCSTFLALGMMPLLLYLYSRGIYDGTL

KDKVPYGSIVISLILILIPCTIGIILNTKRPQYVRYVIKGGTILLILCAI

AVTVLSVLNVGKSILFVMTPHLVATSSLMPFTGFLLGYLLSALFRLNARC

SRTVCMETGCQNVQLCSTILNVTFPPEVIGPLFFFPLLYMLFQLGEGLLF

IAIFRCYEKTKLSKDKMKTISAADSTEETIPTALGNGTHKGEECPPTQPS

VV
```

The inventors have identified a novel HBV preS1-specific receptor playing a key role in Hepatitis B virus (HBV) and/or Hepatitis D virus (HDV) infection, the human sodium taurocholate cotransporter polypeptide NTCP/SLC10A1. Expression of this receptor or of certain non-human counterparts allows to transform cells that were previously unable to bind HBV and/or HDV and/or non-susceptible to HBV and/or HDV infection into cells that are HBV and/or HDV binding-competent and/or susceptible to HBV and/or HDV infection. Cells that are already susceptible to HBV and/or HDV infection (e.g. HepaRG cells) show a significantly increased susceptibility upon expression of NTCP.

Furthermore, an alignment of NTCP/SLC10A1 sequences from various species revealed specific amino acid sequences presumed to be responsible for HBV and/or HDV binding and conferring susceptibility to HBV and/or HDV infection. It is possible to introduce these specific amino acid sequences, e.g. by homologous recombination, into the endogenous NTCP/SLC10A1 genes of cells/organisms exhibiting no or low HBV and/or HDV binding or infection susceptibility in order to confer or increase HBV and/or HDV binding-competence and/or infection susceptibility.

These surprising findings allows the development of HBV and/or HDV-susceptible cells, cell lines and non-human animals that can be used for immunological studies and/or for the screening of drugs, post-entry restriction factors and host dependency factors. Furthermore, the identification of this important receptor will allow the identification of novel compounds that are useful in the treatment of HBV and/or HDV infection.

Reference is now made to the figures, wherein

Figure 2:
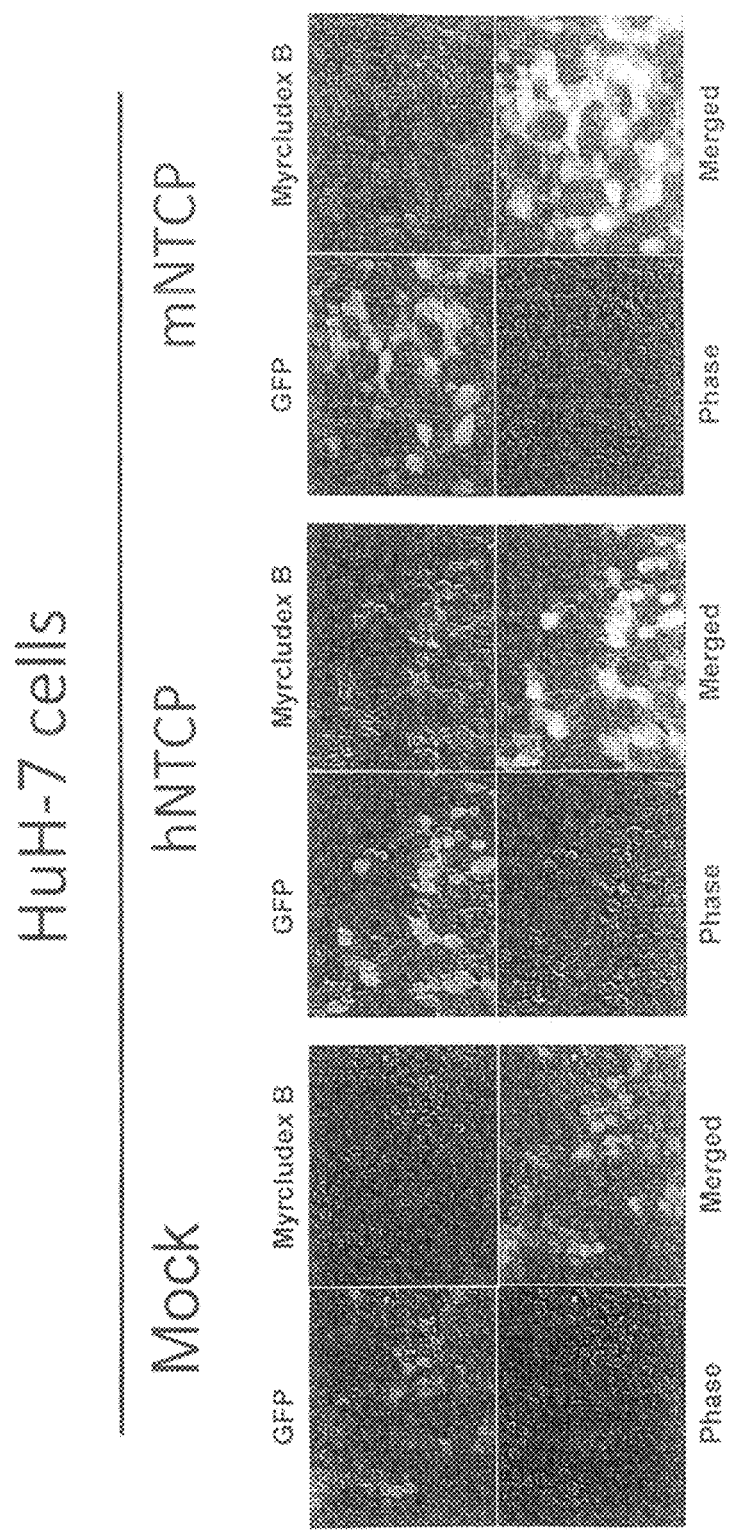
Figure 3:
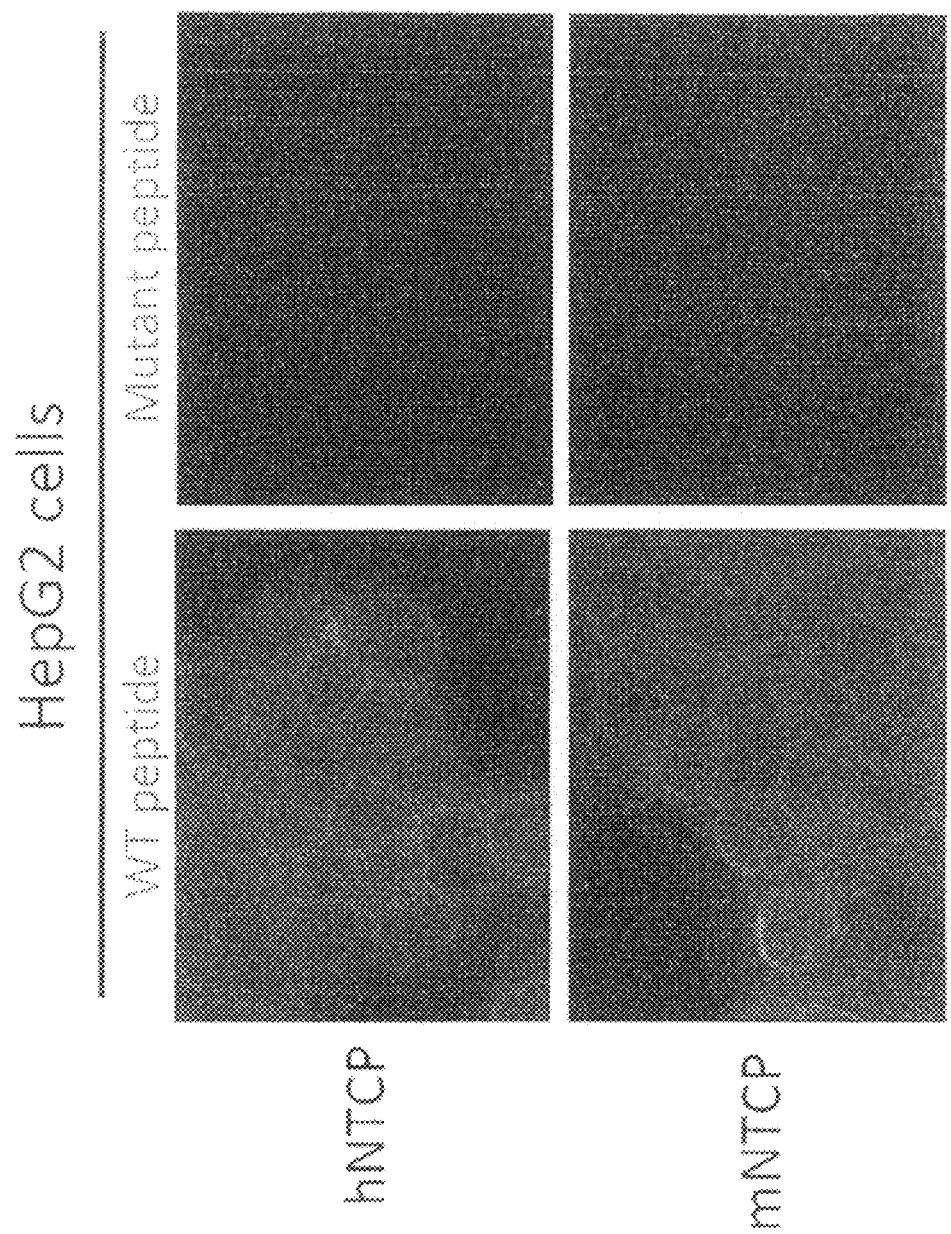
Figure 4:
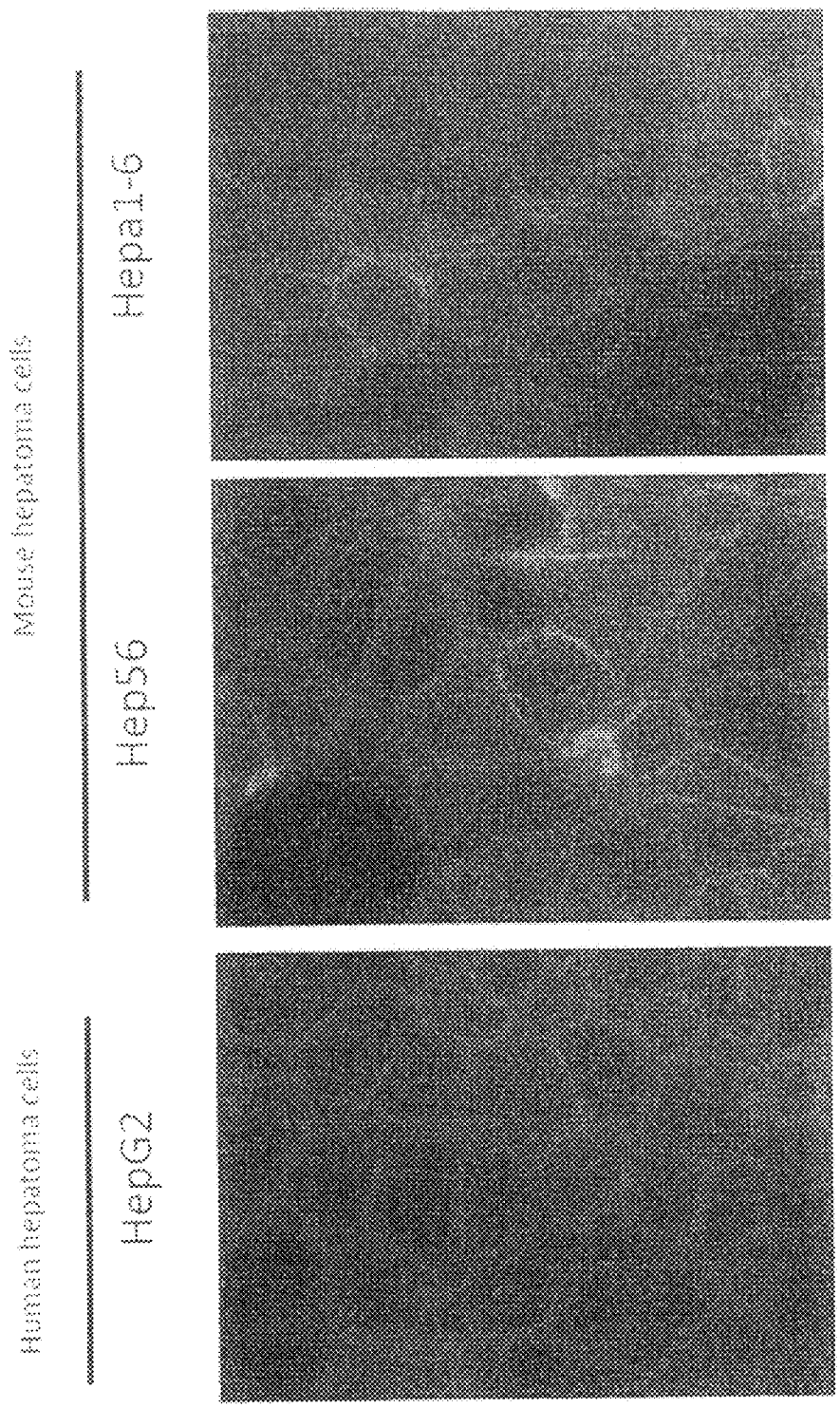
Figure 5:
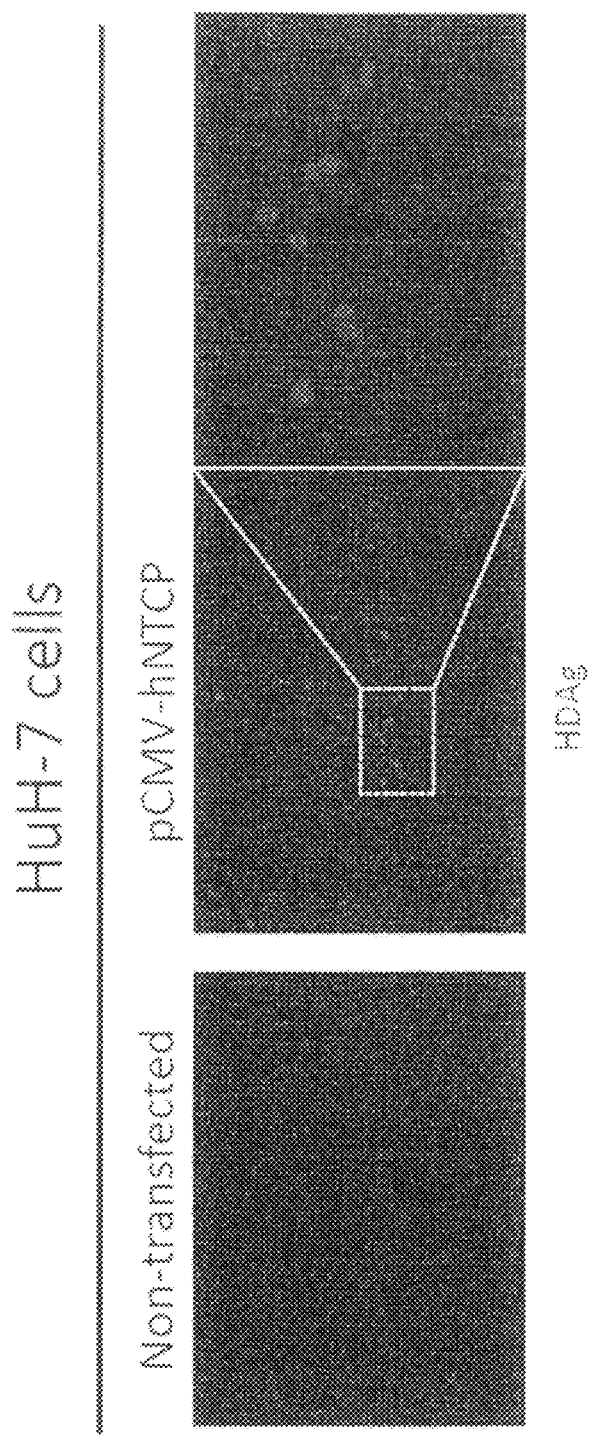
Figure 6:
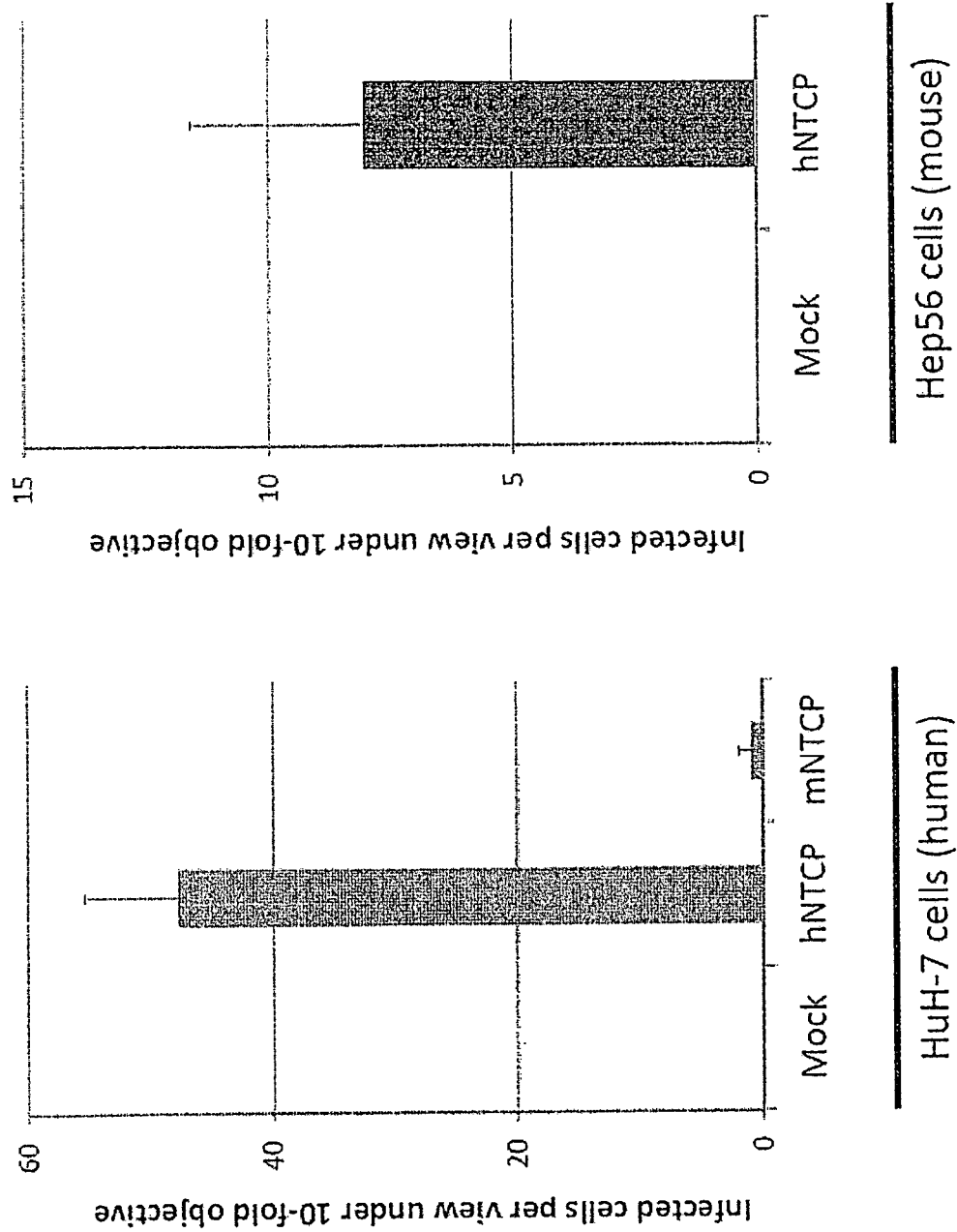
Figure 7:
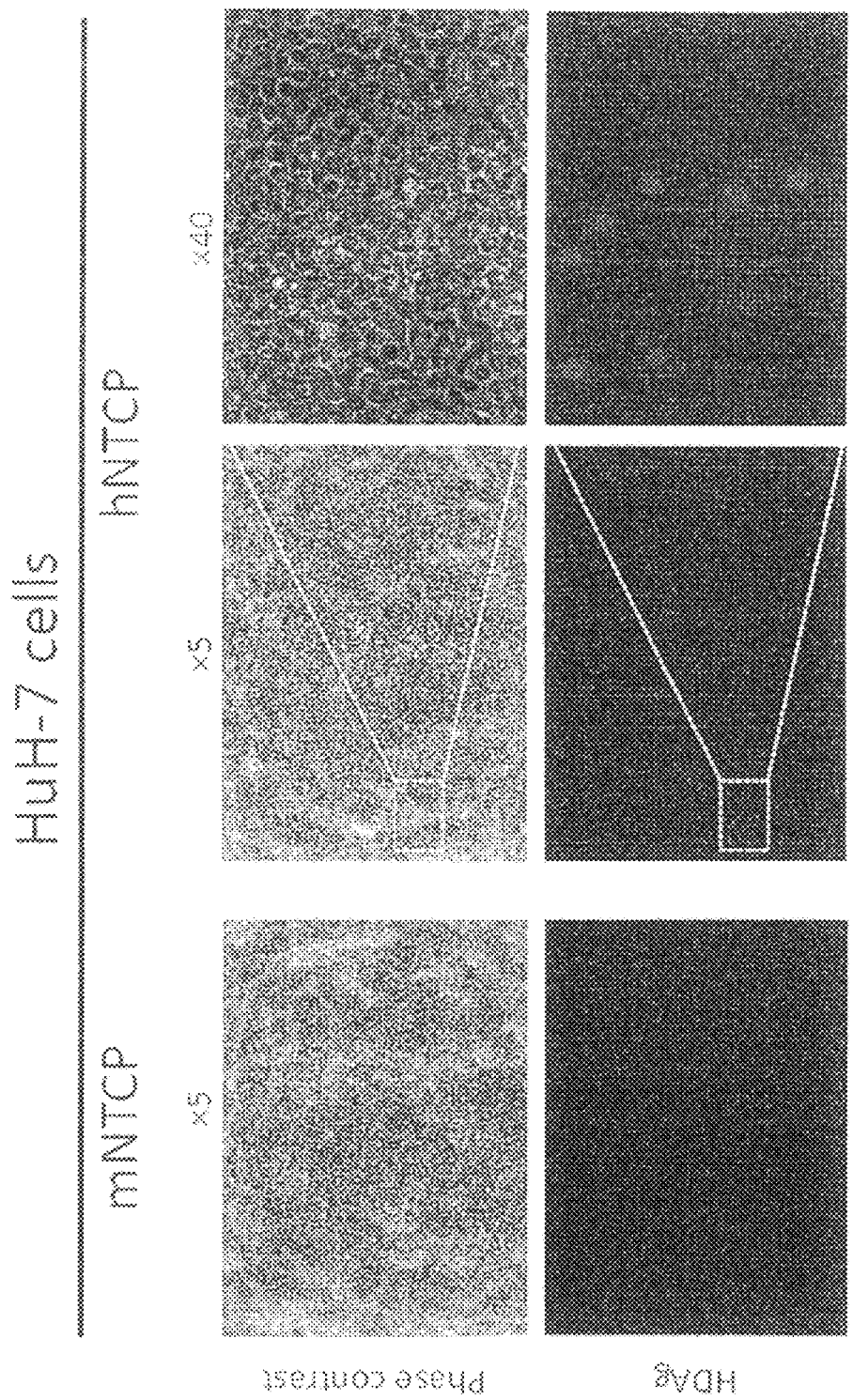
Figure 8:
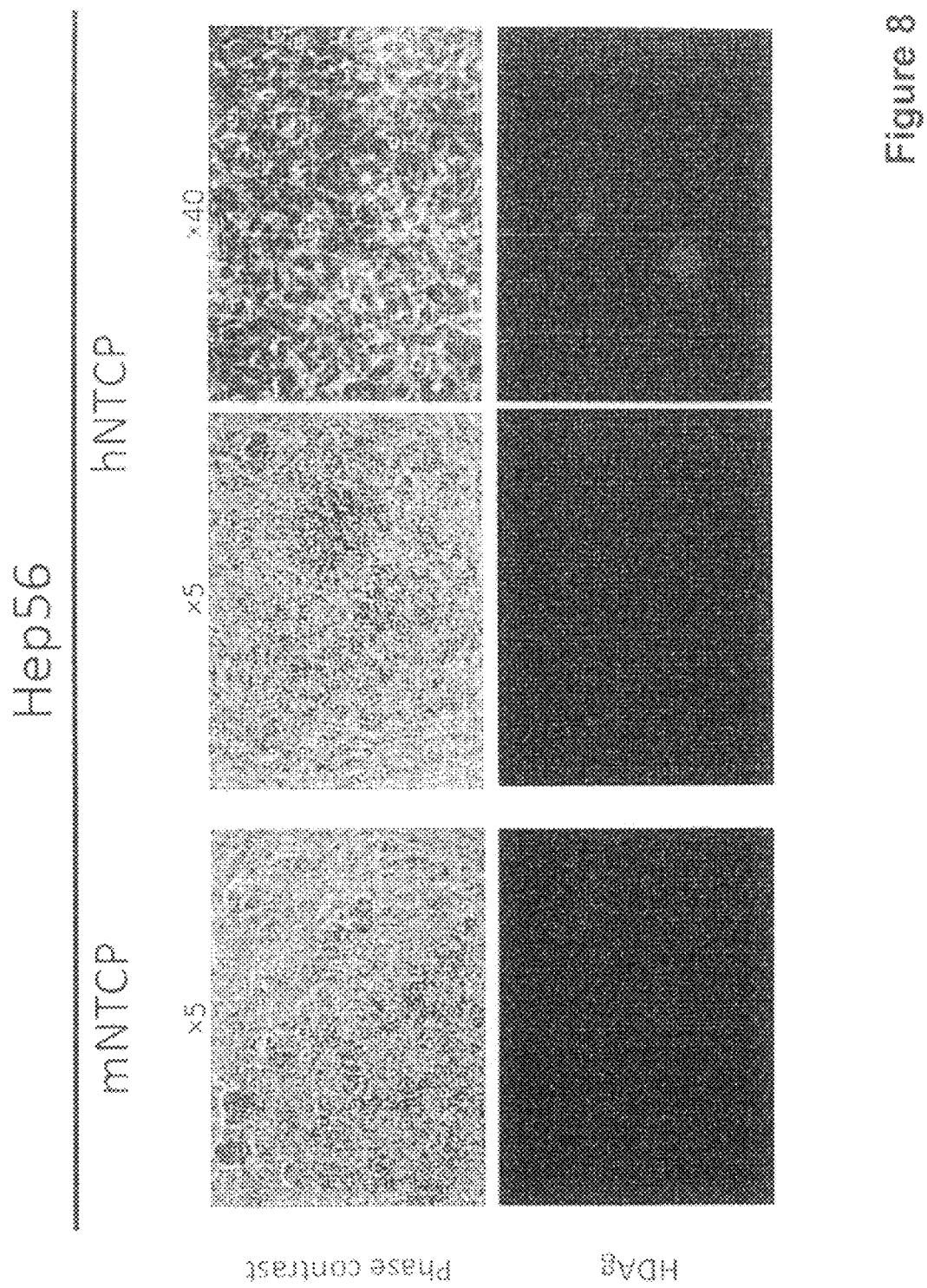

FIG. 1 shows a sequence alignment of the sodium taurocholate co-transporter polypeptide NTCP/SLC10A1 from different species (Human (SEQ ID NO:1); Chimpanzee (SEQ ID NO:3); Orangutan (SEQ ID NO:4); Three shrew (SEQ ID NO:5); Mouse (SEQ ID NO:6); Rat (SEQ ID NO:7); Dog (SEQ ID NO:8); Cynomolgus (SEQ ID NO:9); and Pig (SEQ ID NO: 10)). Species supporting peptide binding and HBV infection (human, chimpanzee, orangutan, and Tupaia belangeri), species that are competent in binding HBV-preS-derived lipopeptides without supporting infection (mouse, rat, dog) and species that are unable to bind and do not support infection are depicted. Identical amino acids are highlighted in yellow. Non conserved amino acid changes are shown without shading. The two amino acids (157 and 158) that differ in the non-binding species cynomolgus and pig (Meier et al., Hepatology 2012; Schieck et al., Hepatology 2012 in press) indicate the essential binding site (highlighted by the box);

FIG. 2 shows that transient transfection of human NTCP and mouse NTCP into HuH7 cells confers binding of an Atto645-labeled HBV preS-lipopeptide (referred to as Myrcludex B, MyrB). HuH7 cells where transiently transfected with a plasmid encoding GFP (left), a plasmids encoding GFP together with human NTCP (middle) and a plasmid encoding GFP and mouse NTCP. 3 days post transfection, cells were incubated with a fluorescently labeled HBV preS-lipopeptide, washed and analyzed by fluorescent microscopy. GFP-fluorescence is shown in the upper left, cells are shown in the lower left, peptide binding is shown in the upper right panel; the merged pictures of transfected and binding competent cells is shown in the lower right panel;

FIG. 3 shows that stably transduced HepG2 cells expressing human or mouse NTCP specifically bind an HBV preS-lipopeptide. HepG2 cells were stably transduced with hNTCP (upper pictures) or mNTCP (lower pictures) and incubated with 500 nM of an Atto-labelled wildtype HBV preS-lipopeptide (left pictures) or the same concentration of a respective mutant peptide with amino acid exchanges in the essential HBV-receptor binding domain (right pictures). Binding of the peptides was visualized by fluorescence microscopy;

FIG. 4 shows that stably transduced mouse hepatoma cells (Hep56.1D and Hepa1-6) specifically bind an HBV preS-lipopeptide. HepG2, Hep56.1D and Hepa1-6 cells were stably transduced with hNTCP and incubated with 500 nM of an Atto-labelled wildtype HBV preS-lipopeptide. Binding of the peptide was visualized by fluorescence microscopy;

FIG. 5 shows that HuH7 cells transfected with human NTCP are susceptible to HDV infection. HuH7 inoculated with a HDV-containing human serum do not show any marker of HDV infection 4 days after inoculation (left picture). Following transfection with a human NTCP expression plasmid an HDV delta antigen-specific staining was observed (right picture);

FIG. 6 shows that endogenous expression of human NTCP in Hep56.1D mouse cell lines renders them susceptible to HDV infection. Hep56.1D mouse hepatoma cell lines alone (mock) or transfected with human NTCP (hNTCP) were infected with an HDV containing serum (right picture). Hepatitis delta antigen expressing cells were counted 5 days post infection. As a second control, human HuH7 cells were transfected with human NTCP or mouse NTCP and infected with HDV (left picture);

FIG. 7 shows that transfection of human but not mouse NTCP renders HuH7 cells susceptible to infection with hepatitis delta virus (HDV). HuH7 cells were transiently transfected with expression vectors encoding mouse NTCP (left panels) or human NTCP (right 4 panels in 2 different magnifications). At confluence, cells were incubated with a patient's serum containing HDV. 4 days after infection cells were stained with an antiserum detecting nuclear delta antigen;

FIG. 8 shows immunofluorescence analysis of NTCP (human) transfected mouse Hep56.1D cells after infection with hepatitis delta virus. Hep56.1D mouse hepatoma cell lines were transfected with mouse NTCP (2 panels on the left) or human NTCP (hNTCP) (4 panels on the right in 2 different magnifications) were infected with an HDV-containing serum and stained with a hepatitis delta antigen specific antibody.

Figure 9:
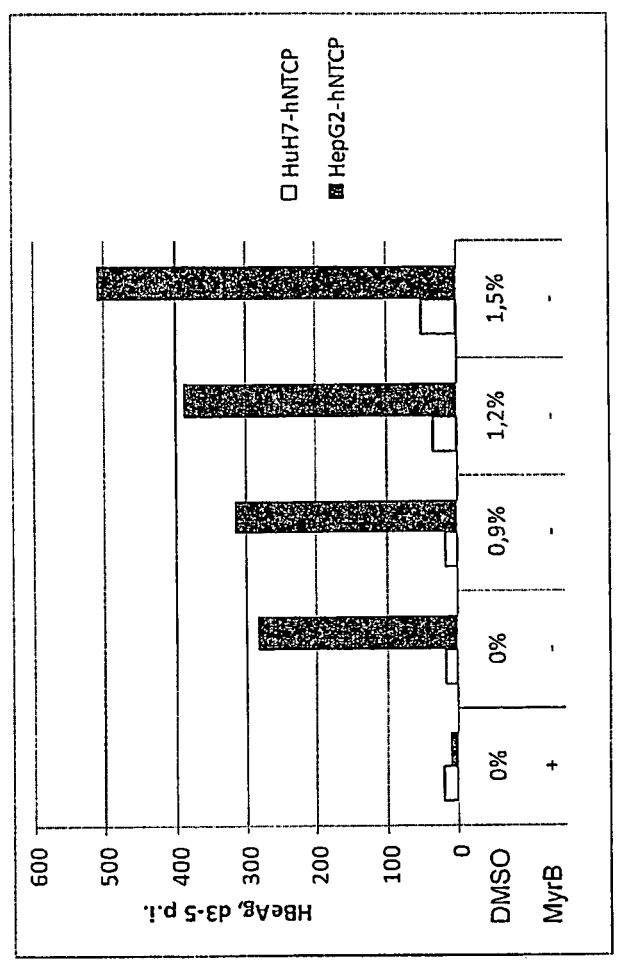

FIG. 9 shows that HepG2 and HuH7 cells stably expressing human NTCP become susceptible to Hepatitis B Virus (HBV) infection. Stably hNTCP transduced HepG2 and HuH7 cell lines were inoculated with HBV at different concentrations of DMSO to induce differentiation processes. Medium was collected on day-5 post infection and HBeAg was quantified. As a specific control for infection an HBV preS-derived lipopeptide (MyrB) was used (left bars). In comparison to HepG2 cells, HuH7 cells produce lower amounts of viral replication markers indicating the presence of a restriction step.

The present invention is now further described by means of the following examples, which are meant to illustrate the present invention, and not to limit its scope.

EXAMPLES

Material & Methods
Sequence of NTCP
The protein sequences of NTCP from different species were obtained from Ensemble (www.ensemble.org).
Alignment
The alignment of NTCP proteins from different species was created by using Vector NTI 9.0 (Invitrogen).
Plasmids and Peptides
The human NTCP (hNTCP) containing construct (pCMV6-XL4-hNTCP) was bought from Origene (USA). The open reading frames of hNTCP and NTCP were amplified by PCR and inserted into pWPIlentiviral vector for transient (pWPI-GFP) or stable expression (pWPI-puro).
The peptide used for inhibition of HBV infection has been described previously as Myrcludex B (MyrB). It is a N-myristoylated peptide comprising the 47 amino acid of HBV L protein. ATTO 645 and ATTO 488 (ATTO-TEC, Germany) are fluorescent dyes used to label the peptide for the binding assay. A mutant peptide with an alanine substitution in the essential binding site (amino acids 11-15) was used as control of the binding specificity.

MyrB
SEQ ID NO: 12
Myr - GTNLSVPNPLGFFPDHQLDPAFGANSNNPDWDFNPNKDHWPEAN
KVG - amide mutant MyrB$^{Ala11-15}$
SEQ ID NO: 13
Myr - GTNLSVPNPAAAAADHQLDPAFGANSNNPDWDFNPNKDHWPEAN
KVG - amide Lentivirus Transduction
To produce recombinant lentiviruses, HEK 293T cells were seeded one day prior transfection. 3 μg of the envelope protein expression construct pczVSV-G, 9 μg of the HIV Gag-Pol expression construct pCMVAR8.74 and 9 μg of the lentiviral vector pWPI were mixed with 25 μg polyethyleneimine before adding to 293T cells. The supernatant containing lentiviral pseudoparticles were harvested and concentrated by ultracentrifugation. The precipitated lentiviral particles were resuspended in cell medium.
For transient expression, hepatic cells were incubated with lentiviruses in the presence of 4% PEG8000. The inoculum was removed after overnight incubation. The cells were washed once with PBS and cultivated for 3 days for expression of the target proteins. For the establishment of stable cell lines, 2.5 μg/ml puromycin was added to select stably transduced cells. Generally, 90% of hepatic cells survived the selection without significant morphological difference compared to untransduced cells.
Cells
Four hepatic cells were used in this work. Two of them are derived from human (HuH-7 and HepG2) and the other two from mouse (Hep56.1D and Hepa1-6). HEK 293T cell were used for lentiviral production.

Binding Assay with Fluorescently Labeled Peptides
To determine the binding competence of hepatocytes, transiently or stably transduced cells were incubated with 200-500 nM fluorescence-labeled peptides in cell medium for 15-60 minutes. Then cells were washed with PBS for 3 times and analyzed by fluorescence microscopy.
HBV and HDV Infection Assay
HBV particles were obtained from HepAD38 cells. For HBV or HDV infection, cells were inoculated with medium containing 4% PEG 8000 and 10-20 μl virus (100× virus stock) overnight at 37° C. Afterwards, cells were washed three times with PBS and further cultivated for 5 days. Presence of the Hepatitis B virus-antigen (HBeAg) secreted into the culture supernatant was determined by Abbott HBeAg assay (Abbott Laboratories). HDV infection was determined by immuno-staining of HDV infected cells with an anti-HDV sera.
Results
The invention of the HepaRG cell line lead to the identification of peptidic receptor ligands derived from the N-terminal preS1-domain of the large (L) viral surface protein, which specifically bind to HBV-susceptible cells and efficiently block infection. Mapping of essential sites within the peptides revealed the requirement of the lipid moiety and the integrity of a conserved sequence 9-NPL-GFFP-15 [SEQ ID NO: 14]. Radioactively and fluorescently labelled peptidic ligands where applied to analyse the bio distribution of the preS/receptor complex mice, rats, dogs, cynomolgus and chimpanzees and the expression patterns and turnover kinetics primary hepatocytes of the respective species or hepatoma cell lines. The results revealed that the receptor: (i) is specifically expressed in liver (ii) becomes induced during differentiation of HepaRG cells, (ii) is down-modulated upon dedifferentiation of PMH and PRH, (iii) shows association with the cytoskeleton allowing little lateral movement within the plasmamembrane, (iv) shows a limited rate of endocytosis (v) is exclusively sorted to the basolateral membrane (vi) conserved binding domain in human, mouse, rat, dog, chimpanzee, but not pig and cynomolgus monkey.
Based on these result the inventors performed a differential affimetrix based expression screen. Up regulated genes in HepaRG-cells undergoing DMSO-induced differentiation were subtracted from to down-regulated genes in PMH during dedifferentiation in the absence of DMSO. The most prominent hits of both screens were combined and subjected to the criteria defined above. Sodium taurocholate cotransporting polypeptide (NTCP, SLC10A1) was the only appropriate candidate meeting these criteria: NTCP, an integral multi-transmembrane protein is exclusively expressed on the basolateral membrane of differentiated hepatocytes. It is scarcely expressed on HepG2, HuH7 and many other hepatoma cell lines. NTCP is instantly induced in HepaRG cells upon DMSO treatment at levels that correspond to the saturation levels of Myrcludex B. It is associated with the cytoskeleton and undergoes slow and regulated (PKC-dependent) endocytosis.
By sequence alignment of NTCP from three groups of hosts (FIG. 1), which differ in their infection and binding competency, the inventors defined two critical amino acids of NTCP (amino acids 157 to 158). The consensus sequence (KG) is present in most susceptible and binding-competent hosts. In contrast, the binding incompetent hosts like cynomolgus monkey and pig do not contain this motif.
The inventors transduced hNTCP or mNTCP into HuH-7 cells and performed a peptide-binding assay (FIG. 2). In comparison to the control with an empty vector (Mock), both human and mouse derived NTCP bind to the peptide.

These signals of bound peptides are correlated to the amount of co-expressed GFP, which indicate the expression level of NTCP.

The inventors further generated four hepatic cells (HuH-7, HepG2, Hep56.1D and Hepa1-6) stably expressing hNTCP or mNTCP. The cells show homogenous binding with the wildtype (WT) peptide but not the mutant peptide (FIG. 3). The mouse hepatoma cells expressing hNTCP or mNTCP show a strong binding to the peptide as well (FIG. 4).

Although the transfection efficacy is low (~20%), HuH-7 cells transfected with hNTCP can be infected by HDV (FIG. 5). The gained susceptibility to HDV infection by hNTCP could also be observed in both human and mouse cells (FIG. 6). Transient transduction of hNTCP confers susceptibility of HuH-7 cell to HDV infection (FIG. 7), whereas the mNTCP protein supporting peptide-binding does not support HDV infection. The mouse cell line Hep56.1D supports HDV infection after transduction with hNTCP (FIG. 8).

The gained susceptibility to HBV infection by NTCP could be observed in HepG2 cells stably expressing hNTCP (FIG. 9). This infection could be specifically inhibited by the peptide Myrcludex B (MyrB) and enhanced by adding DMSO to the cultivation medium. HuH-7 cells expressing hNTCP seem to support HBV infection at a lower level, indicating that an unknown co-factor supporting HBV infection is absent in HuH-7 cells in comparison to HepG2 cells.

The features of the present invention disclosed in the specification, the claims, and/or in the accompanying drawings may, both separately and in any combination thereof, be material for realizing the invention in various forms thereof.

The invention claimed is:

1. A method for producing a cell that is susceptible to Hepatitis B virus (HBV) and/or Hepatitis D Virus (HDV) infection, or has an increased susceptibility to HBV and/or HDV infection, or is able to bind HBV and/or HDV, said method comprising the steps of:
   A) providing a cell that is non-susceptible to HBV and/or HDV infection or has a low susceptibility to HBV and/or HDV infection or is unable to bind HBV and/or HDV:
   B) transducing said cell with a viral vector comprising a nucleic acid sequence encoding:
   an amino acid sequence comprising SEQ ID NO: 1, 3, 4, 5, 6, 7, or 8 or an amino acid sequence that is at least 90% identical to SEQ ID NO: 1, 3, 4, 5, 6, 7, or 8, and an amino acid sequence consisting of the general formula Pro-Tyr-X-Gly-Ile, wherein X is selected from Lys, Arg and Val,
   C) knocking-down one or more endogenous genes of said cell, wherein one of said endogenous genes is the gene encoding the natural sodium taurocholate cotransporter polypeptide (NTCP/SCL10A1) polypeptide of said cell, and said knocking-down one or more endogenous genes of said cell is achieved by means of an shRNA vector; and
   D) culturing the transduced cell in the presence of DMSO when the transduced cell is contacted with HBV and/or HDV.

2. A method for producing a cell that is susceptible to Hepatitis B virus (HBV) and/or Hepatitis D Virus (HDV) infection, or has an increased susceptibility to HBV and/or HDV infection, or is able to bind HBV and/or HDV, said method comprising the steps of:
   A) providing a cell that is non-susceptible to HBV and/or HDV infection or has a low susceptibility to HBV and/or HDV infection or is unable to bind HBV and/or HDV;
   B) transducing said cell with a viral vector comprising a nucleic acid sequence encoding: an amino acid sequence consisting of SEQ ID NO: 2 or an amino acid sequence that is at least 90% identical to SEQ ID NO: 2, and an amino acid sequence comprising the sequence of SEQ ID NO: 1, 3, 4, 5, 6, 7, or 8 or an amino acid sequence that is at least 90% identical to the sequence of SEQ ID NO: 1, 3, 4, 5, 6, 7, or 8,
   C) knocking-down one or more endogenous genes of said cell, wherein one of said endogenous genes is the gene encoding the natural sodium taurocholate cotransporter polypeptide (NTCP/SCL10A1) polypeptide of said cell, and said knocking-down one or more endogenous genes of said cell is achieved by means of an shRNA vector; and
   D) culturing the transduced cell in the presence of DMSO when the transduced cell is contacted with HBV and/or HDV.

3. A method for producing a cell that is susceptible to Hepatitis B virus (HBV) and/or Hepatitis D Virus (HDV) infection, or has an increased susceptibility to HBV and/or HDV infection, or is able to bind HBV and/or HDV, said method comprising the steps of:
   A) providing a cell that is non-susceptible to HBV and/or HDV infection or has a low susceptibility to HBV and/or HDV infection or is unable to bind HBV and/or HDV;
   B) introducing into said cell a nucleic acid sequence encoding:
   an amino acid sequence consisting of SEQ ID NO: 2 or an amino acid sequence that is at least 90% identical to SEQ ID NO: 2, and
   an amino acid sequence comprising the sequence of SEQ ID NO: 1, 3, 4, 5, 6, 7, or 8 or an amino acid sequence that is at least 90% identical to the sequence of SEQ ID NO: 1, 3, 4, 5, 6, 7, or 8.

4. A method for producing a cell that is susceptible to Hepatitis B virus (HBV) and/or Hepatitis D Virus (HDV) infection, or has an increased susceptibility to HBV and/or HDV infection, or is able to bind HBV and/or HDV, said method comprising the steps of:
   A) providing a cell that is non-susceptible to HBV and/or HDV infection or has a low susceptibility to HBV and/or HDV infection or is unable to bind HBV and/or HDV;
   B) introducing into said cell a nucleic acid sequence encoding:
   an amino acid sequence comprising the sequence of SEQ ID NO: 1, 3, 4, 5, 6, 7, or 8, or an amino acid sequence that is at least 90% identical to SEQ ID NO: 1, 3, 4, 5, 6, 7, or 8, and
   an amino acid sequence consisting of the general formula Pro-Tyr-X-Gly-Ile, wherein X is selected from Lys, Arg and Val.

* * * * *

SEQUENCE LISTING

```
<160> NUMBER OF SEQ ID NOS: 15

<210> SEQ ID NO 1
<211> LENGTH: 349
<212> TYPE: PRT
<213> ORGANISM: Homo sapiens

<400> SEQUENCE: 1

Met Glu Ala His Asn Ala Ser Ala Pro Phe Asn Phe Thr Leu Pro Pro
1               5                   10                  15

Asn Phe Gly Lys Arg Pro Thr Asp Leu Ala Leu Ser Val Ile Leu Val
            20                  25                  30

Phe Met Leu Phe Phe Ile Met Leu Ser Leu Gly Cys Thr Met Glu Phe
        35                  40                  45

Ser Lys Ile Lys Ala His Leu Trp Lys Pro Lys Gly Leu Ala Ile Ala
    50                  55                  60

Leu Val Ala Gln Tyr Gly Ile Met Pro Leu Thr Ala Phe Val Leu Gly
65                  70                  75                  80

Lys Val Phe Arg Leu Lys Asn Ile Glu Ala Leu Ala Ile Leu Val Cys
                85                  90                  95

Gly Cys Ser Pro Gly Gly Asn Leu Ser Asn Val Phe Ser Leu Ala Met
            100                 105                 110

Lys Gly Asp Met Asn Leu Ser Ile Val Met Thr Thr Cys Ser Thr Phe
        115                 120                 125

Cys Ala Leu Gly Met Met Pro Leu Leu Leu Tyr Ile Tyr Ser Arg Gly
    130                 135                 140

Ile Tyr Asp Gly Asp Leu Lys Asp Lys Val Pro Tyr Lys Gly Ile Val
145                 150                 155                 160

Ile Ser Leu Val Leu Val Leu Ile Pro Cys Thr Ile Gly Ile Val Leu
                165                 170                 175

Lys Ser Lys Arg Pro Gln Tyr Met Arg Tyr Val Ile Lys Gly Gly Met
            180                 185                 190

Ile Ile Ile Leu Leu Cys Ser Val Ala Val Thr Val Leu Ser Ala Ile
        195                 200                 205

Asn Val Gly Lys Ser Ile Met Phe Ala Met Thr Pro Leu Leu Ile Ala
    210                 215                 220

Thr Ser Ser Leu Met Pro Phe Ile Gly Phe Leu Leu Gly Tyr Val Leu
225                 230                 235                 240

Ser Ala Leu Phe Cys Leu Asn Gly Arg Cys Arg Arg Thr Val Ser Met
                245                 250                 255
```

```
Glu Thr Gly Cys Gln Asn Val Gln Leu Cys Ser Thr Ile Leu Asn Val
            260                 265                 270

Ala Phe Pro Pro Glu Val Ile Gly Pro Leu Phe Phe Phe Pro Leu Leu
            275                 280                 285

Tyr Met Ile Phe Gln Leu Gly Glu Gly Leu Leu Leu Ile Ala Ile Phe
            290                 295                 300

Trp Cys Tyr Glu Lys Phe Lys Thr Pro Lys Asp Lys Thr Lys Met Ile
305                 310                 315                 320

Tyr Thr Ala Ala Thr Thr Glu Glu Thr Ile Pro Gly Ala Leu Gly Asn
            325                 330                 335

Gly Thr Tyr Lys Gly Glu Asp Cys Ser Pro Cys Thr Ala
            340                 345

<210> SEQ ID NO 2
<211> LENGTH: 27
<212> TYPE: PRT
<213> ORGANISM: Homo sapiens

<400> SEQUENCE: 2

Gln Leu Cys Ser Thr Ile Leu Asn Val Ala Phe Pro Pro Glu Val Ile
1               5                   10                  15

Gly Pro Leu Phe Phe Phe Pro Leu Leu Tyr Met
            20                  25

<210> SEQ ID NO 3
<211> LENGTH: 349
<212> TYPE: PRT
<213> ORGANISM: Pan troglodytes (Chimpanzee)

<400> SEQUENCE: 3

Met Glu Ala His Asn Val Ser Ala Pro Phe Asn Phe Thr Leu Pro Pro
1               5                   10                  15

Asn Phe Gly Lys Arg Pro Thr Asp Leu Ala Leu Ser Val Ile Leu Val
            20                  25                  30

Phe Met Leu Phe Phe Ile Met Leu Ser Leu Gly Cys Thr Met Glu Phe
            35                  40                  45

Ser Lys Ile Lys Ala His Leu Trp Lys Pro Lys Gly Leu Ala Ile Ala
    50                  55                  60

Leu Val Ala Gln Tyr Gly Ile Met Pro Leu Thr Ala Phe Val Leu Gly
65                  70                  75                  80

Lys Val Phe Arg Leu Lys Asn Ile Glu Ala Leu Ala Ile Leu Val Cys
            85                  90                  95

Gly Cys Ser Pro Gly Gly Asn Leu Ser Asn Val Phe Ser Leu Ala Met
            100                 105                 110

Lys Gly Asp Met Asn Leu Ser Ile Val Met Thr Thr Cys Ser Thr Phe
            115                 120                 125

Cys Ala Leu Gly Met Met Pro Leu Leu Leu Tyr Ile Tyr Ser Arg Gly
            130                 135                 140

Ile Tyr Asp Gly Asp Leu Lys Asp Lys Val Pro Tyr Lys Gly Ile Val
145                 150                 155                 160

Ile Ser Leu Val Leu Val Leu Ile Pro Cys Thr Ile Gly Ile Val Leu
                165                 170                 175

Lys Ser Lys Arg Pro Gln Tyr Met Arg Tyr Val Ile Lys Gly Gly Met
            180                 185                 190

Ile Ile Ile Leu Leu Cys Ser Val Ala Val Thr Val Leu Ser Ala Ile
            195                 200                 205
```

```
Asn Val Gly Lys Ser Ile Met Phe Ala Met Thr Pro Leu Leu Ile Ala
    210                 215                 220

Thr Ser Ser Leu Met Pro Phe Ile Gly Phe Leu Leu Gly Tyr Val Leu
225                 230                 235                 240

Ser Ala Leu Phe Cys Leu Asn Gly Arg Cys Arg Arg Thr Val Ser Met
                245                 250                 255

Glu Thr Gly Cys Gln Asn Val Gln Leu Cys Ser Thr Ile Leu Asn Val
            260                 265                 270

Ala Phe Pro Pro Glu Val Ile Gly Pro Leu Phe Phe Pro Leu Leu
        275                 280                 285

Tyr Met Ile Phe Gln Leu Gly Glu Gly Leu Leu Leu Ile Ala Met Phe
    290                 295                 300

Trp Cys Tyr Glu Lys Phe Lys Thr Pro Lys Asp Lys Thr Lys Met Thr
305                 310                 315                 320

Tyr Thr Ala Ala Thr Thr Glu Glu Thr Ile Pro Gly Ala Leu Gly Asn
                325                 330                 335

Gly Thr Tyr Lys Gly Glu Asp Cys Ser Pro Cys Thr Ala
            340                 345

<210> SEQ ID NO 4
<211> LENGTH: 349
<212> TYPE: PRT
<213> ORGANISM: Pongo pygmaeus

<400> SEQUENCE: 4

Met Glu Ala His Asn Ala Ser Ala Pro Phe Asn Phe Thr Leu Pro Pro
1               5                   10                  15

Asn Phe Gly Lys Arg Pro Thr Asp Leu Ala Leu Ser Val Ile Leu Val
                20                  25                  30

Phe Met Leu Phe Phe Ile Met Leu Ser Leu Gly Cys Thr Met Glu Phe
            35                  40                  45

Ser Lys Ile Lys Ala His Leu Trp Lys Pro Lys Gly Leu Ala Ile Ala
        50                  55                  60

Leu Val Ala Gln Tyr Gly Ile Met Pro Leu Thr Ala Phe Val Leu Gly
65                  70                  75                  80

Lys Val Phe Arg Leu Lys Asn Ile Glu Ala Leu Ala Ile Leu Val Cys
                85                  90                  95

Gly Cys Ser Pro Gly Gly Asn Leu Ser Asn Val Phe Ser Leu Ala Met
                100                 105                 110

Lys Gly Asp Met Asn Leu Ser Ile Val Met Thr Thr Cys Ser Thr Phe
            115                 120                 125

Cys Ala Leu Gly Met Met Pro Leu Leu Leu Tyr Ile Tyr Ser Arg Gly
        130                 135                 140

Ile Tyr Asp Gly Asp Leu Lys Asp Lys Val Pro Tyr Arg Gly Ile Val
145                 150                 155                 160

Ile Ser Leu Val Leu Val Leu Ile Pro Cys Thr Ile Gly Ile Val Leu
                165                 170                 175

Lys Ser Lys Arg Pro Gln Tyr Met Arg Tyr Val Ile Lys Gly Gly Met
                180                 185                 190

Ile Ile Ile Leu Leu Cys Ser Val Ala Val Thr Val Leu Ser Ala Ile
            195                 200                 205

Asn Val Gly Lys Ser Ile Met Phe Ala Met Thr Pro Leu Leu Ile Ala
    210                 215                 220

Thr Ser Ser Leu Met Pro Phe Ile Gly Phe Leu Leu Gly Tyr Val Leu
225                 230                 235                 240
```

Ser Ala Leu Phe Cys Leu Asn Gly Arg Cys Arg Arg Thr Val Ser Met
            245                 250                 255

Glu Thr Gly Cys Gln Asn Val Gln Leu Cys Ser Thr Ile Leu Asn Val
            260                 265                 270

Ala Phe Pro Pro Glu Val Ile Gly Pro Leu Phe Phe Pro Leu Leu
            275                 280                 285

Tyr Met Ile Phe Gln Leu Gly Glu Gly Leu Leu Leu Ile Ala Met Phe
            290                 295                 300

Trp Cys Tyr Glu Lys Phe Lys Thr Pro Lys Gly Lys Thr Lys Met Ile
305                 310                 315                 320

Tyr Thr Ala Ala Thr Thr Glu Glu Thr Ile Pro Gly Ala Leu Gly Asn
            325                 330                 335

Gly Thr Tyr Lys Gly Glu Asp Cys Ser Pro Cys Thr Ala
            340                 345

<210> SEQ ID NO 5
<211> LENGTH: 349
<212> TYPE: PRT
<213> ORGANISM: Tupaia belangeri

<400> SEQUENCE: 5

Met Glu Ala His Asn Leu Ser Ala Pro Leu Asn Phe Thr Leu Pro Pro
1               5                   10                  15

Asn Phe Gly Lys Arg Pro Thr Asp Gln Ala Leu Ser Val Ile Leu Val
            20                  25                  30

Val Met Leu Leu Ile Met Met Leu Ser Leu Gly Cys Thr Met Glu Phe
            35                  40                  45

Ser Lys Ile Lys Ala His Phe Trp Lys Pro Lys Gly Leu Ala Ile Ala
            50                  55                  60

Leu Leu Ala Gln Tyr Gly Ile Met Pro Leu Thr Ala Phe Ala Leu Gly
65              70                  75                  80

Lys Val Phe Pro Leu Asn Asn Ile Glu Ala Leu Ala Ile Leu Val Cys
                85                  90                  95

Gly Cys Ser Pro Gly Gly Asn Leu Ser Asn Val Phe Ser Leu Ala Met
            100                 105                 110

Lys Gly Asp Met Asn Leu Ser Ile Val Met Thr Thr Cys Ser Thr Phe
            115                 120                 125

Phe Ala Leu Gly Met Met Pro Leu Leu Leu Tyr Ile Tyr Ser Lys Gly
            130                 135                 140

Ile Tyr Asp Gly Asp Leu Lys Asp Lys Val Pro Tyr Val Gly Ile Val
145                 150                 155                 160

Ile Ser Leu Ile Leu Val Leu Ile Pro Cys Thr Ile Gly Ile Phe Leu
                165                 170                 175

Lys Ser Lys Arg Pro Gln Tyr Val Pro Tyr Val Thr Lys Ala Gly Met
            180                 185                 190

Ile Ile Ile Leu Leu Leu Ser Val Ala Ile Thr Val Leu Ser Val Ile
            195                 200                 205

Asn Val Gly Lys Ser Ile Met Phe Val Met Thr Pro His Leu Leu Ala
            210                 215                 220

Thr Ser Ser Leu Met Pro Phe Ile Gly Phe Leu Leu Gly Tyr Ile Leu
225                 230                 235                 240

Ser Thr Leu Phe Arg Leu Asn Ala Gln Cys Ser Arg Thr Val Ser Met
                245                 250                 255

Glu Thr Gly Cys Gln Asn Val Gln Leu Cys Ser Thr Ile Leu Asn Val

```
                        260                 265                 270
Thr Phe Arg Pro Glu Val Ile Gly Pro Leu Phe Phe Phe Pro Leu Leu
            275                 280                 285

Tyr Met Ile Phe Gln Leu Gly Glu Gly Leu Leu Leu Ile Ala Ile Tyr
            290                 295                 300

Arg Cys Tyr Glu Lys Ile Lys Pro Ser Lys Asp Lys Thr Lys Val Ile
305                 310                 315                 320

Tyr Thr Ala Ala Lys Thr Glu Glu Thr Ile Pro Gly Thr Leu Gly Asn
            325                 330                 335

Gly Thr Tyr Lys Gly Glu Glu Cys Ser Pro Gly Thr Ala
            340                 345

<210> SEQ ID NO 6
<211> LENGTH: 362
<212> TYPE: PRT
<213> ORGANISM: Mus musculus

<400> SEQUENCE: 6

Met Glu Ala His Asn Val Ser Ala Pro Phe Asn Ser Leu Pro Pro
1               5                   10                  15

Gly Phe Gly His Arg Ala Thr Asp Thr Ala Leu Ser Val Ile Leu Val
            20                  25                  30

Val Met Leu Leu Leu Ile Met Leu Ser Leu Gly Cys Thr Met Glu Phe
        35                  40                  45

Ser Lys Ile Lys Ala His Phe Trp Lys Pro Lys Gly Val Ile Ile Ala
    50                  55                  60

Ile Val Ala Gln Tyr Gly Ile Met Pro Leu Ser Ala Phe Leu Leu Gly
65                  70                  75                  80

Lys Val Phe His Leu Thr Ser Ile Glu Ala Leu Ala Ile Leu Ile Cys
            85                  90                  95

Gly Cys Ser Pro Gly Gly Asn Leu Ser Asn Leu Phe Thr Leu Ala Met
                100                 105                 110

Lys Gly Asp Met Asn Leu Ser Ile Val Met Thr Thr Cys Ser Ser Phe
            115                 120                 125

Thr Ala Leu Gly Met Met Pro Leu Leu Leu Tyr Ile Tyr Ser Lys Gly
        130                 135                 140

Ile Tyr Asp Gly Asp Leu Lys Asp Lys Val Pro Tyr Lys Gly Ile Met
145                 150                 155                 160

Leu Ser Leu Val Met Val Leu Ile Pro Cys Ala Ile Gly Ile Phe Leu
            165                 170                 175

Lys Ser Lys Arg Pro His Tyr Val Pro Tyr Val Leu Lys Ala Gly Met
                180                 185                 190

Ile Ile Thr Phe Ser Leu Ser Val Ala Val Thr Val Leu Ser Val Ile
            195                 200                 205

Asn Val Gly Asn Ser Ile Met Phe Val Met Thr Pro His Leu Leu Ala
        210                 215                 220

Thr Ser Ser Leu Met Pro Phe Thr Gly Phe Leu Met Gly Tyr Ile Leu
225                 230                 235                 240

Ser Ala Leu Phe Arg Leu Asn Pro Ser Cys Arg Arg Thr Ile Ser Met
            245                 250                 255

Glu Thr Gly Phe Gln Asn Val Gln Leu Cys Ser Thr Ile Leu Asn Val
                260                 265                 270

Thr Phe Pro Pro Glu Val Ile Gly Pro Leu Phe Phe Phe Pro Leu Leu
            275                 280                 285
```

```
Tyr Met Ile Phe Gln Leu Ala Glu Gly Leu Leu Phe Ile Ile Ile Phe
    290                 295                 300

Arg Cys Tyr Leu Lys Ile Lys Pro Gln Lys Asp Gln Thr Lys Ile Thr
305                 310                 315                 320

Tyr Lys Ala Ala Ala Thr Glu Asp Ala Thr Pro Ala Ala Leu Glu Lys
                325                 330                 335

Gly Thr His Asn Gly Asn Asn Pro Pro Thr Gln Pro Gly Leu Ser Pro
                340                 345                 350

Asn Gly Leu Asn Ser Gly Gln Met Ala Asn
            355                 360

<210> SEQ ID NO 7
<211> LENGTH: 362
<212> TYPE: PRT
<213> ORGANISM: Rattus norvegicus

<400> SEQUENCE: 7

Met Glu Val His Asn Val Ser Ala Pro Phe Asn Phe Ser Leu Pro Pro
1               5                   10                  15

Gly Phe Gly His Arg Ala Thr Asp Lys Ala Leu Ser Ile Ile Leu Val
                20                  25                  30

Leu Met Leu Leu Leu Ile Met Leu Ser Leu Gly Cys Thr Met Glu Phe
            35                  40                  45

Ser Lys Ile Lys Ala His Leu Trp Lys Pro Lys Gly Val Ile Val Ala
    50                  55                  60

Leu Val Ala Gln Phe Gly Ile Met Pro Leu Ala Ala Phe Leu Leu Gly
65                  70                  75                  80

Lys Ile Phe His Leu Ser Asn Ile Glu Ala Leu Ala Ile Leu Ile Cys
                85                  90                  95

Gly Cys Ser Pro Gly Gly Asn Leu Ser Asn Leu Phe Thr Leu Ala Met
                100                 105                 110

Lys Gly Asp Met Asn Leu Ser Ile Val Met Thr Thr Cys Ser Ser Phe
            115                 120                 125

Ser Ala Leu Gly Met Met Pro Leu Leu Leu Tyr Val Tyr Ser Lys Gly
    130                 135                 140

Ile Tyr Asp Gly Asp Leu Lys Asp Lys Val Pro Tyr Lys Gly Ile Met
145                 150                 155                 160

Ile Ser Leu Val Ile Val Leu Ile Pro Cys Thr Ile Gly Ile Val Leu
                165                 170                 175

Lys Ser Lys Arg Pro His Tyr Val Pro Tyr Ile Leu Lys Gly Gly Met
                180                 185                 190

Ile Ile Thr Phe Leu Leu Ser Val Ala Val Thr Ala Leu Ser Val Ile
            195                 200                 205

Asn Val Gly Asn Ser Ile Met Phe Val Met Thr Pro His Leu Leu Ala
    210                 215                 220

Thr Ser Ser Leu Met Pro Phe Ser Gly Phe Leu Met Gly Tyr Ile Leu
225                 230                 235                 240

Ser Ala Leu Phe Gln Leu Asn Pro Ser Cys Arg Arg Thr Ile Ser Met
                245                 250                 255

Glu Thr Gly Phe Gln Asn Ile Gln Leu Cys Ser Thr Ile Leu Asn Val
            260                 265                 270

Thr Phe Pro Pro Glu Val Ile Gly Pro Leu Phe Phe Phe Pro Leu Leu
    275                 280                 285

Tyr Met Ile Phe Gln Leu Ala Glu Gly Leu Leu Ile Ile Ile Ile Phe
290                 295                 300
```

Arg Cys Tyr Glu Lys Ile Lys Pro Pro Lys Asp Gln Thr Lys Ile Thr
305                 310                 315                 320

Tyr Lys Ala Ala Ala Thr Glu Asp Ala Thr Pro Ala Ala Leu Glu Lys
            325                 330                 335

Gly Thr His Asn Gly Asn Ile Pro Pro Leu Gln Pro Gly Pro Ser Pro
        340                 345                 350

Asn Gly Leu Asn Ser Gly Gln Met Ala Asn
        355                 360

<210> SEQ ID NO 8
<211> LENGTH: 392
<212> TYPE: PRT
<213> ORGANISM: Canis familiaris

<400> SEQUENCE: 8

Met Asp Ala Pro Asn Ile Thr Ala Pro Leu Asn Phe Thr Leu Pro Pro
1               5                   10                  15

Asn Phe Gly Lys Arg Pro Thr Asp Lys Ala Leu Ser Ile Ile Leu Val
            20                  25                  30

Phe Leu Leu Ile Ile Met Leu Ser Leu Gly Cys Thr Met Glu Phe
        35                  40                  45

Ser Lys Ile Lys Ala His Phe Trp Lys Pro Lys Gly Leu Val Ile Ala
    50                  55                  60

Leu Ile Ala Gln Tyr Gly Ile Met Pro Leu Thr Ala Phe Thr Leu Gly
65                  70                  75                  80

Lys Val Phe Arg Leu Asn Asn Ile Glu Ala Leu Ala Ile Leu Val Cys
                85                  90                  95

Gly Cys Ser Pro Gly Gly Thr Leu Ser Asn Val Phe Ser Leu Ala Met
            100                 105                 110

Lys Gly Asp Met Asn Leu Ser Ile Val Met Thr Thr Cys Ser Thr Phe
        115                 120                 125

Phe Ala Leu Gly Met Met Pro Leu Leu Leu Tyr Ile Tyr Ser Asn Gly
    130                 135                 140

Ile Tyr Asp Gly Asp Leu Lys Asp Lys Val Pro Tyr Lys Gly Ile Val
145                 150                 155                 160

Ser Ser Leu Val Leu Val Leu Ile Pro Cys Thr Ile Gly Ile Phe Leu
                165                 170                 175

Lys Ala Lys Arg Pro Gln Tyr Val Arg Tyr Ile Lys Lys Gly Gly Met
            180                 185                 190

Ile Ile Met Leu Leu Leu Ser Val Ala Ile Thr Ala Leu Ser Val Ile
        195                 200                 205

Asn Val Gly Lys Ser Ile Arg Phe Val Met Thr Pro His Leu Leu Ala
    210                 215                 220

Thr Ser Ser Leu Met Pro Phe Ile Gly Phe Leu Leu Gly Tyr Ile Leu
225                 230                 235                 240

Ser Ala Leu Phe Arg Leu Asp Gly Arg Cys Ser Arg Thr Val Ser Met
                245                 250                 255

Glu Thr Gly Cys Gln Asn Val Gln Leu Cys Ser Thr Ile Leu Asn Val
            260                 265                 270

Thr Phe Pro Pro Glu Val Ile Gly Pro Leu Phe Phe Phe Pro Leu Leu
        275                 280                 285

Tyr Met Ile Phe Gln Leu Gly Glu Gly Val Phe Leu Ile Ser Ile Phe
    290                 295                 300

Arg Cys Tyr Glu Lys Ile Lys Pro Ser Lys Asp Lys Thr Lys Met Ile

```
                305                 310                 315                 320
Tyr Thr Ala Ala Ala Thr Glu Glu Ile Thr Pro Gly Ala Leu Gly Asn
                    325                 330                 335
Gly Thr His Lys Gly Glu Glu Cys Ser Pro Cys Thr Ala Ala Pro Ser
                340                 345                 350
Pro Ser Gly Leu Asp Ser Gly Lys Ala Ile Gln Cys Asp Gln Leu
            355                 360                 365
Glu Lys Ala Lys Asp Lys Arg Asn Thr Lys Glu Ser Phe Ser Ser
370                 375                 380
Ile Gly Ser Ser Asn Tyr Gln Asn
385                 390

<210> SEQ ID NO 9
<211> LENGTH: 349
<212> TYPE: PRT
<213> ORGANISM: Macaca fascicularis

<400> SEQUENCE: 9

Met Glu Ala His Asn Ala Ser Ala Pro Phe Asn Phe Thr Leu Pro Pro
1               5                   10                  15
Asn Phe Gly Lys Arg Pro Thr Asp Leu Ala Leu Ser Ile Ile Leu Val
                20                  25                  30
Phe Met Leu Phe Phe Val Met Leu Ser Leu Gly Cys Thr Met Glu Phe
            35                  40                  45
Ser Lys Ile Lys Ala His Leu Trp Lys Pro Lys Gly Leu Ala Ile Ala
        50                  55                  60
Leu Val Ala Gln Tyr Gly Ile Met Pro Leu Thr Ala Phe Val Leu Gly
65                  70                  75                  80
Lys Val Phe Gln Leu Asn Asn Ile Glu Ala Leu Ala Ile Leu Val Cys
                85                  90                  95
Gly Cys Ser Pro Gly Gly Asn Leu Ser Asn Val Phe Ser Leu Ala Met
                100                 105                 110
Lys Gly Asp Met Asn Leu Ser Ile Val Met Thr Thr Cys Ser Thr Phe
            115                 120                 125
Cys Ala Leu Gly Met Met Pro Leu Leu Leu Tyr Leu Tyr Thr Arg Gly
        130                 135                 140
Ile Tyr Asp Gly Asp Leu Lys Asp Lys Val Pro Tyr Gly Arg Ile Ile
145                 150                 155                 160
Leu Ser Leu Val Pro Val Leu Ile Pro Cys Thr Ile Gly Ile Val Leu
                165                 170                 175
Lys Ser Lys Arg Pro Gln Tyr Met Arg Tyr Val Ile Lys Gly Gly Met
            180                 185                 190
Ile Ile Ile Leu Leu Cys Ser Val Ala Val Thr Val Leu Ser Ala Ile
        195                 200                 205
Asn Val Gly Lys Ser Ile Met Phe Ala Met Thr Pro Leu Leu Ile Ala
        210                 215                 220
Thr Ser Ser Leu Met Pro Phe Ile Gly Phe Leu Leu Gly Tyr Val Leu
225                 230                 235                 240
Ser Ala Leu Phe Cys Leu Asn Gly Arg Cys Arg Arg Thr Val Ser Met
                245                 250                 255
Glu Thr Gly Cys Gln Asn Val Gln Leu Cys Ser Thr Ile Leu Asn Val
            260                 265                 270
Ala Phe Pro Pro Glu Val Ile Gly Pro Leu Phe Phe Phe Pro Leu Leu
        275                 280                 285
```

```
Tyr Met Ile Phe Gln Leu Gly Glu Gly Leu Leu Ile Ala Met Phe
    290                 295                 300

Arg Cys Tyr Glu Lys Phe Lys Thr Pro Lys Asp Lys Thr Lys Met Ile
305                 310                 315                 320

Tyr Thr Ala Ala Thr Thr Glu Glu Thr Ile Pro Gly Ala Leu Gly Asn
                325                 330                 335

Gly Thr Tyr Lys Gly Glu Asp Cys Ser Pro Cys Thr Ala
                340                 345

<210> SEQ ID NO 10
<211> LENGTH: 352
<212> TYPE: PRT
<213> ORGANISM: Sus scrofa

<400> SEQUENCE: 10

Met Glu Ala Leu Asn Glu Ser Ala Pro Ile Asn Phe Thr Leu Pro His
1               5                   10                  15

Asn Phe Gly Lys Arg Pro Thr Asp Leu Ala Leu Ser Val Ile Leu Val
                20                  25                  30

Phe Met Leu Leu Ile Ile Met Leu Ser Leu Gly Cys Thr Met Glu Phe
            35                  40                  45

Gly Arg Ile Arg Ala His Phe Arg Lys Pro Lys Gly Leu Ala Ile Ala
        50                  55                  60

Leu Val Ala Gln Tyr Gly Ile Met Pro Leu Thr Ala Phe Ala Leu Gly
65                  70                  75                  80

Lys Leu Phe Arg Leu Asn Asn Val Glu Ala Leu Ala Ile Leu Ile Cys
                85                  90                  95

Gly Cys Ser Pro Gly Gly Asn Leu Ser Asn Ile Phe Ala Leu Ala Met
                100                 105                 110

Lys Gly Asp Met Asn Leu Ser Ile Met Met Thr Thr Cys Ser Thr Phe
            115                 120                 125

Leu Ala Leu Gly Met Met Pro Leu Leu Leu Tyr Leu Tyr Ser Arg Gly
130                 135                 140

Ile Tyr Asp Gly Thr Leu Lys Asp Lys Val Pro Tyr Gly Ser Ile Val
145                 150                 155                 160

Ile Ser Leu Ile Leu Ile Leu Ile Pro Cys Thr Ile Gly Ile Ile Leu
                165                 170                 175

Asn Thr Lys Arg Pro Gln Tyr Val Arg Tyr Val Ile Lys Gly Gly Thr
                180                 185                 190

Ile Leu Leu Ile Leu Cys Ala Ile Ala Val Thr Val Leu Ser Val Leu
            195                 200                 205

Asn Val Gly Lys Ser Ile Leu Phe Val Met Thr Pro His Leu Val Ala
210                 215                 220

Thr Ser Ser Leu Met Pro Phe Thr Gly Phe Leu Leu Gly Tyr Leu Leu
225                 230                 235                 240

Ser Ala Leu Phe Arg Leu Asn Ala Arg Cys Ser Arg Thr Val Cys Met
                245                 250                 255

Glu Thr Gly Cys Gln Asn Val Gln Leu Cys Ser Thr Ile Leu Asn Val
                260                 265                 270

Thr Phe Pro Pro Glu Val Ile Gly Pro Leu Phe Phe Phe Pro Leu Leu
            275                 280                 285

Tyr Met Leu Phe Gln Leu Gly Glu Gly Leu Leu Phe Ile Ala Ile Phe
        290                 295                 300

Arg Cys Tyr Glu Lys Thr Lys Leu Ser Lys Asp Lys Met Lys Thr Ile
305                 310                 315                 320
```

```
Ser Ala Ala Asp Ser Thr Glu Glu Thr Ile Pro Thr Ala Leu Gly Asn
                325                 330                 335

Gly Thr His Lys Gly Glu Glu Cys Pro Pro Thr Gln Pro Ser Val Val
            340                 345                 350

<210> SEQ ID NO 11
<211> LENGTH: 5
<212> TYPE: PRT
<213> ORGANISM: Artificial Sequence
<220> FEATURE:
<223> OTHER INFORMATION: binding region of HBV
<220> FEATURE:
<221> NAME/KEY: misc_feature
<222> LOCATION: (3)..(3)
<223> OTHER INFORMATION: Xaa can be Lys, Arg and Val

<400> SEQUENCE: 11

Pro Tyr Xaa Gly Ile
1               5

<210> SEQ ID NO 12
<211> LENGTH: 7
<212> TYPE: PRT
<213> ORGANISM: Homo sapiens

<400> SEQUENCE: 12

Gly Met Ile Ile Ile Leu Leu
1               5

<210> SEQ ID NO 13
<211> LENGTH: 47
<212> TYPE: PRT
<213> ORGANISM: Hepatitis B virus

<400> SEQUENCE: 13

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Lys Val Gly
        35                  40                  45

<210> SEQ ID NO 14
<211> LENGTH: 47
<212> TYPE: PRT
<213> ORGANISM: Artificial Sequence
<220> FEATURE:
<223> OTHER INFORMATION: mutant MyrB(Ala11-15)

<400> SEQUENCE: 14

Gly Thr Asn Leu Ser Val Pro Asn Pro Ala Ala Ala Ala Ala Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Lys Val Gly
        35                  40                  45

<210> SEQ ID NO 15
<211> LENGTH: 7
<212> TYPE: PRT
<213> ORGANISM: Hepatitis B virus

<400> SEQUENCE: 15
```

```
Asn Pro Leu Gly Phe Phe Pro
1               5
```